United States Patent
Xiang et al.

(10) Patent No.: US 7,704,923 B2
(45) Date of Patent: *Apr. 27, 2010

(54) HIGH THROUGHPUT SCREENING OF CATALYSTS USING SPIN RESONANCE

(75) Inventors: Xiao-Dong Xiang, Danville, CA (US); Haitao Yang, San Jose, CA (US); Gang Wang, San Jose, CA (US); Jonathan Melman, Redwood City, CA (US)

(73) Assignee: Intematix Corporation, Fremont, CA (US)

( * ) Notice: Subject to any disclaimer, the term of this patent is extended or adjusted under 35 U.S.C. 154(b) by 480 days.

This patent is subject to a terminal disclaimer.

(21) Appl. No.: 11/299,034

(22) Filed: Dec. 8, 2005

(65) Prior Publication Data

US 2006/0160136 A1    Jul. 20, 2006

Related U.S. Application Data

(60) Provisional application No. 60/634,780, filed on Dec. 8, 2004.

(51) Int. Cl.
C40B 30/00 (2006.01)
(52) U.S. Cl. ............................................. 506/7; 73/579
(58) Field of Classification Search ........................ None
See application file for complete search history.

(56) References Cited

U.S. PATENT DOCUMENTS 6,173,604 B1    1/2001  Xiang et al.
6,426,226 B1 *  7/2002  Senkan ........................ 506/11
6,532,806 B1    3/2003  Xiang et al.
7,109,706 B2    9/2006  Xiang et al.

OTHER PUBLICATIONS

Longo et al., IEEE Transactions on Microwave Theory and Techniques 41(1):117-122 (1993).*
Hunger et al., Angew. Chem. Int. Ed. 40:2954-2971 (2001).*
Caplus Accession No. 1972-481870, index for Vigoureux et al. (Comptes Rendus des Seances de I'Academie Sciences, Serie B: Sciences Physiques, 1972, vol. 275, No. 2, pp. 57-60.
Albrecht, T.R. et al., Frequency modulation detection using high-$Q$ cantilevers for enhanced force microscope sensitivity, J. Appl. Phys., Jan. 15, 1991, pp. 668-673, 69 (2), American Institute of Physics.
Durig, U. et al., Logarithmic current-to-voltage converter for local probe microscopy, Rev. Sci. Instrum., Oct. 1997, pp. 3814-3816, 68 (10), American Institute of Physics.
Weyand, K., An NMR marginal oscillator for measuring magnetic fields below 50 mT, Instrumentation and Measurement, IEEE Transactions on, Apr. 1989, pp. 410-414, vol. 38, No. 2, IEEE.

* cited by examiner

*Primary Examiner*—Jeffrey S. Lundgren
(74) *Attorney, Agent, or Firm*—Fliesler Meyer LLP

(57) ABSTRACT

High throughput screening of catalyst libraries may be performed using spin resonance techniques, and an evanescent wave probe developed by the present inventors. The probe may operate using either nuclear magnetic resonance or electron spin resonance techniques. In one configuration, a scanning evanescent wave spin resonance probe is used in conjunction with a library of catalysts or other materials, and localized detection of spin resonance is carried out at each library address. In another configuration, the evanescent wave probe is used in a micro-reactor array assay.

8 Claims, 32 Drawing Sheets

Catalyst Library

HIGH THROUGHPUT SCREENING OF CATALYSTS USING SPIN RESONANCE

CROSS REFERENCE TO RELATED APPLICATIONS

This application claims priority to U.S. Provisional Application Ser. No. 60/634,780 by inventors Xiao-Dong Xiang and Haitao Yang, filed Dec. 8, 2004, titled "High throughput screening of catalysts for catalytic reactions using electron spin resonance." U.S. Provisional Application Ser. No. 60/634,780 is hereby incorporated herein in its entirety.

BACKGROUND OF THE INVENTION

1. Field of the Invention

Embodiments of the present invention are directed to the use electron spin resonance (ESR) and nuclear magnetic resonance (NMR) spectroscopy for high throughput catalyst screening assays. Catalysts may comprise individual members of a catalyst library. Embodiments of the present invention are also directed to the screening of members of an array of micro-reactors.

2. State of the Art

High throughput screening of catalysts presents tremendous opportunities to rapidly develop more efficient catalysts for a vast variety of catalytic reactions in the chemical industries, pharmaceutical industries, and bio-medical industries. Currently, infrared spectroscopy (IR), mass spectroscopy (MS), and gas chromatography (GC) in combination with micro-reactors or library assays have been developed for this purpose.

ESR spectroscopy has proven to be very useful for characterizing radical reactions. Most catalytic reactions involve intermediate radical reactions. Due to un-paired electrons present during radical reactions, electron spin resonance of those un-paired electrons give rise to intrinsic and rich information about catalytic reactions, such as reaction site, rate and detailed mechanism. In the past, however, ESR technology would only allow for the measurement of large amounts of samples, materials, or specimens, and only in a specific environment. What is needed is a high throughput screening assay capable of handling large numbers of specimens and samples in small quantities. To the inventors' knowledge, such an assay has not heretofore been possible, nor have any solutions to the problem even been proposed.

Such needed techniques are contemplated by the present inventors to encompass both ESR and NMR technologies.

SUMMARY

High throughput screening of catalyst libraries may be performed using spin resonance techniques, and an evanescent wave probe developed by the present inventors. The probe may operate using either nuclear magnetic resonance or electron spin resonance techniques. In one configuration, a scanning evanescent wave spin resonance probe is used in conjunction with a library of catalysts or other materials, and localized detection of spin resonance is carried out at each library address. In another configuration, the evanescent wave probe is used in a micro-reactor array assay.

The present embodiments include an evanescent wave probe configured to detect spin resonance from at least one member of an array of catalysts in a catalyst library. The evanescent wave probe may detect spin resonance that is either electron spin resonance (ESR), or nuclear magnetic resonance (NMR). Alternatively, the evanescent wave probe may be configured to detect spin resonance from at least one member of an array of micro-reactors in a micro-reactor library. Similarly, the detected spin resonance from individual reactors in a library of micro-reactors may be either electron spin resonance (ESR) or nuclear magnetic resonance (NMR).

BRIEF DESCRIPTION OF THE DRAWINGS

FIG. 21A represents the shear force mode with tuning fork mounted horizontally; FIG. 21B represents the normal atomic force mode with tuning fork mounted vertically;

DETAILED DESCRIPTION OF THE INVENTION

An ESR and NMR probe that has been developed by the present applicants, and that is capable of spatial resolution and extremely high sensitivity, has made it possible to provide a high throughput, spin resonance screening assay. The details of this spin resonance probe are described in subsequent sections of this disclosure. A first section describes how an evanescent wave probe incorporates one or more of spin resonance detection, impedance detection, and/or atomic force microscopy. A second section gives further details about how the present evanescent wave probe techniques may be used in conjunction with scanning tunneling microscopy to detect nuclear and/or electron spin resonance. A third section gives further details of high resolution and high sensitivity detection and/or profiling of the electromagnetic impedance of a substance using an evanescent wave probe.

High Throughout Screening of Catalysts Using Spin Resonance

Figure 1:
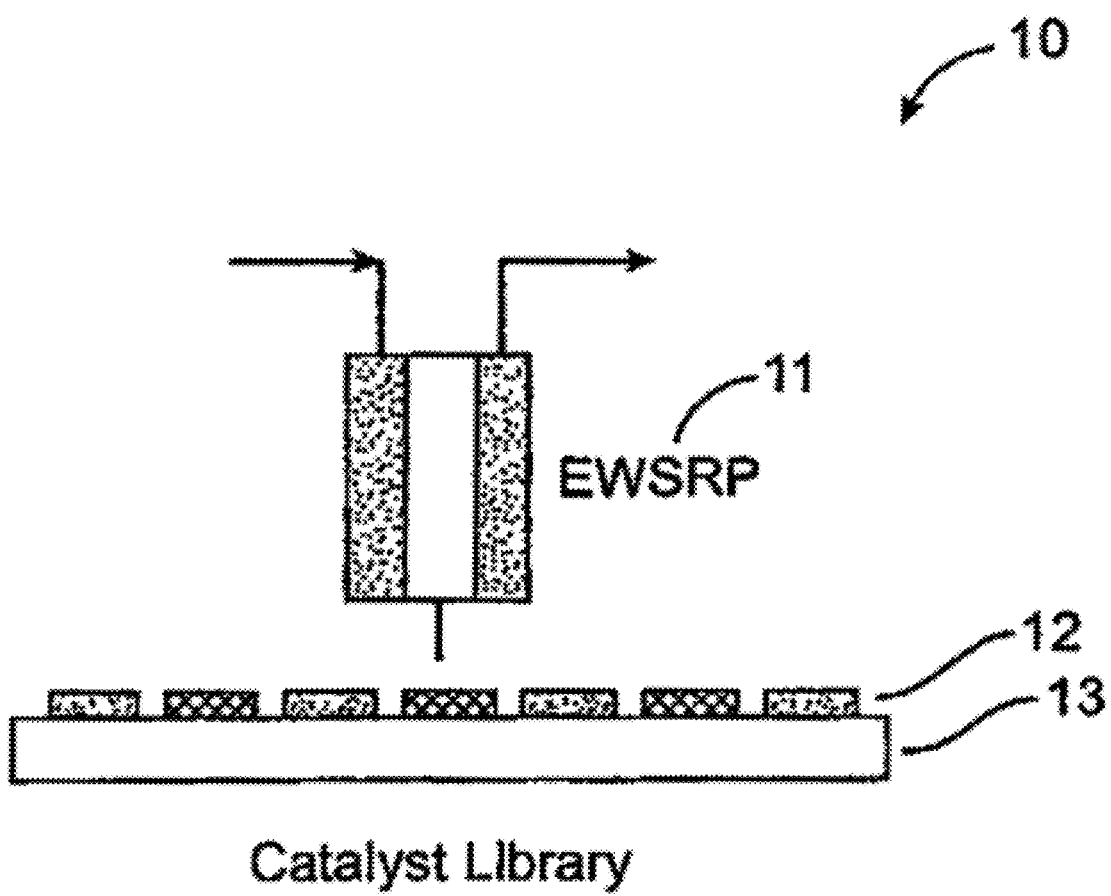
FIG. 1 is a schematic of one embodiment of the present invention, the schematic showing how an evanescent wave spin resonance probe (EWSRP) may be used to screen a catalyst library in a surface scanning assay.

In one embodiment of the present invention, evanescent wave spin resonance probe (EWSRP) may be used to screen a catalyst library in a surface scanning assay, as illustrated generally at reference numeral 10 in FIG. 1. In this configuration, a scanning evanescent wave spin resonance probe 11 (EWSRP) is used for localized detection of electron spin resonance spectroscopy. A library of catalysts 12, in particle or thin film format, is coated on a solid support 13. Each catalyst member has a specific location or address in the library 12, and may or may not be situated in a different reaction environment. Each member of the catalyst library 12 is scanned by the EWSRP 11. Since the catalytic activity is located on the surface of catalysts, the localized detection will eliminate error signals and can be qualified through calibration. The supporting materials (such as solid support 13) are typically non-metallic and non-magnetic materials. Since the spin resonance detection may be performed at a variety of gas pressures, and measurements made over a wide range of temperatures, this surface screening assay can be performed in the realistic and/or real time reaction conditions of a variety of environments. This is particularly true of high pressure gas environments.

Figure 2:
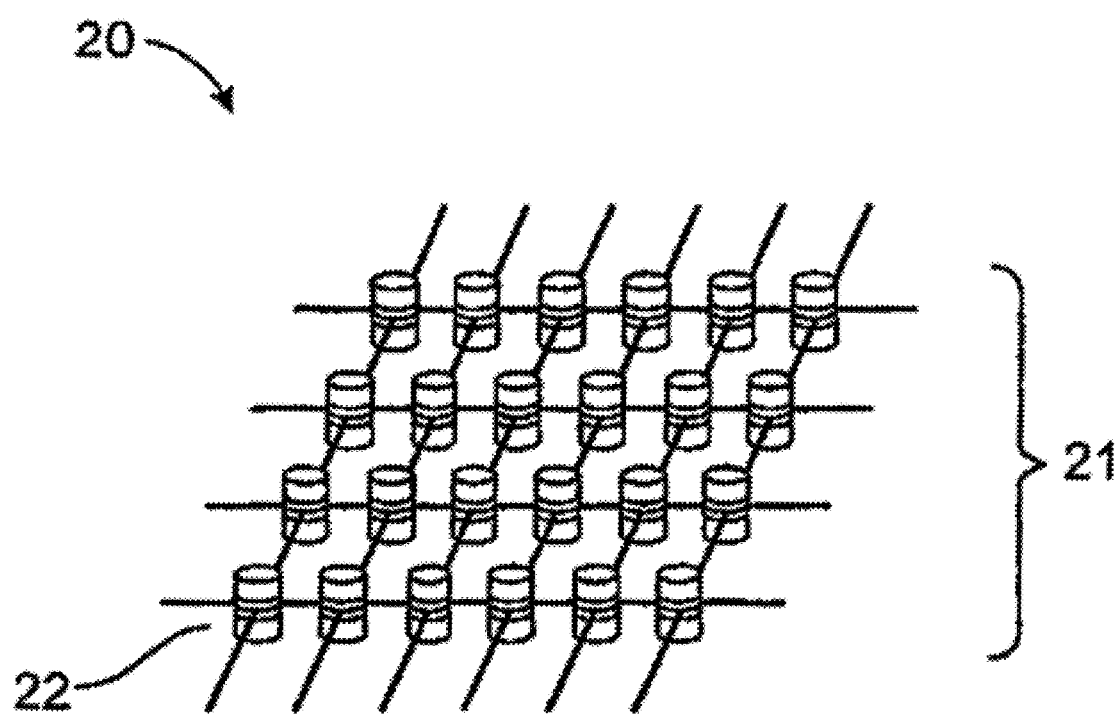
FIG. 2 is a schematic of another embodiment of the present invention, the schematic showing how catalysts may be screened in a high throughput assay when the catalysts are part of a micro-reactor array.

In an alternative embodiment, an evanescent wave probe is used in a micro-reactor array assay. This embodiment is shown generally at reference numeral 20 in FIG. 2. Referring to FIG. 2, an array of micro-reactors 21 made of non-metallic and non-magnetic materials contains catalysts and reactants at desired liquid pressure and temperature in each of the micro-reactors, one of which has been shown at reference numeral 22. Each reactor is wounded with a micro-coil for inductive detection. A evanescent wave resonator probe (not shown) connected a data acquisition system (not shown) may be sequentially connected to a micro-coil to measure spin resonance during the reactions taking place in each reactor. In this case, the beginning of a reaction is synchronized with data acquisition. In a different configuration, an equal number of resonator detectors are permanently connected to the micro-coils. The data acquisition system is then connected to each detector by a switching system. In this array, high pressure, high temperature liquid-based reactions may be assayed.

Nuclear Magnetic Resonance and Libraries

NMR is a useful tool for determining changes in the chemical environment of the nuclei being examined. NMR can be used in many different ways, for example, it can be used to examine the depletion of a starting material, examine the formation of a product, and track the kinetics of one or more competing reactions in a system. Typically, these tasks are accomplished by examining the area under a resonance peak at a given chemical shift. NMR can also be used to determine information about the structure of a product and the level and nature of impurities.

For the analysis of reaction products, NMR can be used as a method of molecular weight determination for polymers. The ratio of the integration of peaks resulting from end groups to the integration of peaks resulting from internal groups can be used to calculate the molecular weight and the number molecular weight. Additionally, tacticity and degree of branching can also be determined from the NMR, allowing determination of the quality of the polymer obtained, in addition to the size of the polymer.

Because the polymer grows at the surface of the catalyst (and often from the surface of the catalyst), spatially addressable NMR can be used to determine the spectrum of polymer grown at a particular entry in the catalyst library. This correlation of polymer spectrum to the catalyst used, enables high throughput screening a library of polymerization catalysts. Additionally, the spatial resolution allows direct comparison of the intensity of specific polymer resonances between different library entries. A key for this type of screening, is that unlike most polymerizations, where a termination/quenching step ends the reaction, and polymer is quantified by gel permeation chromatography, here, the library is simply removed from the monomer containing solution, which allows the polymers to remain linked to the catalytic site.

The 1H NMR technique is favored over 13C, as the natural abundance of 13C is ~1%, while the natural abundance of 1H is ~99.9%. Unless isotopically labeled starting materials are used, the small scale on which this technique will be operated and the low natural abundance of 13C and 15N, makes these nuclei less attractive to scan for. As appropriate, other common NMR active nuclei can be used, such as, but not limited to, 19F and 31P.

In one embodiment of this technique, the formation of polyethylene from ethylene can be measured. The local depletion of ethylene may be tracked by a decrease of the resonance peak at 5.4 ppm in the 1H spectrum, while the formation of polyethylene can also be tracked; the resonance of the end group (—C$\underline{H}$3) typically appears around 1.1 ppm, while internal groups (—C$\underline{H}$2-) appear around 1.5 ppm. The resonance of the methylene group attached to the catalyst (cat-C$\underline{H}$2-) will show shifting and possibly broadening based on its attachment to a center, which may be paramagnetic. As the ratio of —CH2- to —CH3 increases in the polymer chain, the ratio of the integration of the two resonance peaks will increase, but not always linearly, due to hardware limitations. For example, at library entry #1, the ratio of the 1.5 ppm peak to the 1.1 ppm peak is 100:1 and the intensity of the 1.5 ppm peak is 1000 arbitrary units. At library entry #2, the ratio of the two peaks is 30:1 and the intensity of the 1.5 ppm peak is 200 arbitrary units. At library entry #3, the ratio of the two peaks is 500:1 and the intensity of the 1.5 ppm peak is 500 arbitrary units. At library entry #4, the ratio of the two peaks is 1:1 and the intensity of the 1.5 ppm peak is 100 arbitrary units. Such results could be interpreted as entry #1 is the most active catalyst, catalyzing the production of the most polymer, while entry #3 is not as active, however, it catalyzes longer chain growth. Entry #2 produces polymer neither as quickly nor as lengthy as entries #1 and #3. Entry #4 is barely active as a catalyst.

In another embodiment of this technique, the formation of polymethylmethacrylate can be examined. The monomer, methylmethacrylate exhibits resonant peaks at 1.9, 3.7, and a doublet centered at 5.8 ppm. The doublet at 5.8 arise from the hydrogen nuclei of the methacrylate's terminal methylene group (=C$\underline{H}$2). As the monomer polymerizes, the terminal methylene resonances decrease as polymerization occurs. A library entry to library entry comparison of the relative intensities of the pendant ester peak (—C(O)—O—C$\underline{H}$3) at 3.6 ppm can give information about the amount of polymer formed, while the chemical shift of the pendant methyl peak (polymer backbone-C$\underline{H}$3), in addition to giving information about the amount of polymer, also gives information about the tacticity of the chains formed, with syndiotactic giving a peak at 0.9 ppm and isotactic giving a peak at 1.2 ppm. Also, the chemical shifts of the polymer backbone methylene units (—C$\underline{H}$2-) can give information about amounts and tacticity of the polymer chains formed. In the syndiotactic polymer, the methylene shift is seen at 1.9 ppm, while in the isotactic, this peak is split into a doublet of doublets centered at 1.9 (in a 500 MHz machine, the resonance appears as a doublet at 1.6 ppm and a doublet at 2.3 ppm). The end group, which can be used to determine the molecular weight of a chain, can have a resonance at 1.7 ppm.

Electron Spin Resonance and Libraries

Electron Spin Resonance (or Electron Paramagnetic Resonance), ESR (or EPR), is used to probe the nature of unpaired electron spins in materials. The resonant frequency is related to the environment around the unpaired spin, both the nature of the nucleus, including oxidation state and the chemical environment surrounding the atom. As such, much information can be garnered by examining the resonance frequency and splitting. The unpaired electron or electrons may be centered on any atom, or shared between more than one atom. Such entities can come from, but are not limited to the following elements: N, P, As, Cl, Br, I, C, $O_2$, Cu, Ni, Co, Fe, Mn, Cr, V, and Ti. By using the small probe outlined here, much information can be garnered from a library.

This methodology can be used to probe library entries for any spins as the library entry changes during the course of catalysis. Catalysis typically operates by electron exchange between the catalyst and the substrate. In the process, unpaired electron spins can be created either on the catalyst, the substrate or both, the environment around existing unpaired spins can change, or unpaired spins can be paired up, causing the resonance signal to disappear.

Spin labels are also commonly used help determine the structure of proteins and other biomacromolecules. Typically, compounds containing a stable nitroxide radical and having functionality showing affinity for specific sites on the biomacromolecule. Often a cysteine residue is used as the point of attachment of the spin label. Such attached labels can give real-time solution phase information about the structure, folding, stacking, etc. of large biomolecules, which is just as important for understanding function as the chain sequence. The spin label can also be attached to an enzyme factor or co-factor to help elucidate information about the enzyme's active site.

In one embodiment, the well known Wacker process for the oxidation of alkenes by dioxygen with a catalyst pairing can be probed by ESR. A library of combinations of metals, will show creation of spin at library entries which have catalytic activity, such as Pd(II)/Cu(II), where the copper oscillates between Cu(II) and Cu(I)

In another embodiment, the library is composed of possible co-factors for an enzymatic reaction, each with a spin label attached. In a solution of enzyme and factor, a change in ESR signal can be observed when the enzyme reacts with the co-factor, enabling discovery of which co-factors will function in the enzymatic process.

In another contemplated embodiment, the library is composed of spin labeled potential biomarkers. When the library is exposed to particular types cells, biomarkers matching those on the cell membranes will experience a change in the ESR signal of the attached spin label, giving information about the receptors on the cell membrane. For example, spin labeled folate would show a change in signal when exposed to breast cancer cells, which over-express folate receptors.

Library Screening in General

The present techniques may be used for high throughput screening of combinatorially synthesized compounds to identify specific chemical bonding and other spin resonance related signatures in the compounds.

Accurate measurement of the resonance frequency can be used to monitor small changes in specimen magnetization (magnetic moment/volume), magnetic anisotropy, mechanical strain (magneto-restriction) and/or shape anisotropy. Magnetization and magnetic anisotropy are also very sensitive to temperature, and FMR probes have been investigated for use as thermometers. The peak of the resonance line is also proportional to the ratio of magnetization to intrinsic line width (for a Lorentzian shape spectrum). As such it sensitively characterizes variations in chemical composition, structural homogeneity, and polaronic charge from the magnitude of the circuit Q and the degree of Gossip line broadening.

Another important application is the detection of small (nm to μm size) ferromagnetic, super-paramagnetic, or light-pumped spin-populated semiconductor particles. These particles can be used, for example as fluorescent particles, in bioscience, as tagging particles (when the appropriate chemical bonding is used to link the particle with molecules, pathogens, DNA's, proteins and other biological reagents) and/or as contrast agents to diagnose or to identify structure, activity and other biological properties. Examples of magnetic particles suitable for this use include those disclosed in U.S. Provisional Patent Application No. 60/447,097, filed on Feb. 13, 2003, the entire contents of which are herein incorporated by reference.

For this application, high sensitivity of the detection technique is extremely important. Because room temperature detection is crucial, high spin population of the particles and long spin relaxation time at room temperature are also important. Choice of materials for the tagging particles is, therefore, also important. The criteria for particle materials are narrow spin resonance (i.e., long relaxation), high g factor, non-metallic and high ferromagnetic magnetization at room temperature. The high Q made possible by the narrow-line width specimens such as highest purity Yttrium Ion Garnet (YIG), YIG substituted with aluminum, gallium or indium, or certain spinel compounds such as lithium ferrite, are examples of suitable choices for the particle materials. Furthermore, changes in (narrow) line widths can also be used to sense changes induced by adsorbed magnetic molecules on the surface or chemical bonding. For this application, the largest practical surface-to-volume ratio is desirable. Ferrite materials, such as YIG, also have the advantages of non-air sensitive as in metallic particles, and robust ferromagnetic properties as particles size decreases. A ferrite molecule is attached to at least one molecule whose presence or absence in a collection of molecules is of interest, and a selected portion of the collection is interrogated using spatially resolved spin resonance detection. If spin resonance (1) is detected or (2) is not detected, this condition is interpreted as indicating that (1) the molecule of interest is present or (2) the molecule of interest is present, if at all, in a concentration that is below a detection threshold for the spin resonance detection, respectively.

Advantages of using detection of spin resonance of small particles, such as YIG or lithium ferrite, include the following: (1) Discrimination between specific bonding and non-specific bonding. Magnetic force of ferromagnetic particles and influence of spin resonance frequency (field) can all be used to discriminate between of specific and non-specific bonding; (2) Because different materials have different spin resonance (frequency-magnetic field relationship), this technique will provide "multi-color" capability as in a luminescent tagging technique. This response is in contrast to the magnetization detection technique for simple magnetic particle tagging, where only one property, magnetization, is measured and cannot be used to distinguish different types of tagging particles or agents.

The exemplary embodiments of spatially resolved NMR described herein are a powerful tool for determining the structure of organic chemicals, especially the structure of protein, proteomics targets or polypeptides. An example application is the high throughput screening of the structure of proteins. Examples of preferred biological or chemical samples are selected from a group consisting of proteomics, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides; organic and inorganic compounds in fluid or condensed matter forms.

The spatially resolved NMR described in the exemplary embodiments herein has the advantage of providing imaging and spectroscopy simultaneously. Different information in the NMR spectrum can be used to calculate the structure of proteins: the chemical shifts, the peak splitting patterns and the intensities of the resonant peaks. Conventional simulation techniques can be used for the calculation of the structure through the spectrum. In order to get 1D, 2D and 3D structure of the target proteins, the protein is labeled in different ways in order to get more spectrum information. Conventional NMR labeling material can be used, such as $^{15}N^-$, $^{13}C^-$, $^2H^-$, $^1H^-$ or any of their combination.

Protein structure determination is important in several ways. The structures confirm the evolutionary changes in the primary structure of a given protein from related species, which lead to genetic disorder and diseases at the molecular level. Clear understanding of the nature of these diseases depends upon precise structure determination of the concerned proteins. Also, when the structure of an enzyme is determined, a suitable inhibitor of the active site can be designed through combinatorial chemistry, computer modeling and docking techniques. This structure based drug design promises efficient drugs for several diseases, in a short time. The function of a protein is directly linked to its 3-D structure, which has been proved by several lines of examples and evidences. Highly resolved structures can lead to very clear understanding of the functions of these molecules. The structure function relationship is the key to our knowledge of biology and the biological world.

The Evanescent Wave Probe that may be used to Investigate Addresses of a Library For many applications in materials and bioscience research, and this case interrogating the individual members of a library, spatially resolved spin resonance detection with high sensitivity is desired. The members of the library may be catalysts, or the addresses of the library may comprise any kinds of materials.

Conventional spin resonance detection experiments are usually performed by placing a sample in a microwave cavity or a pair of RF coils situated in a strong DC or substantially static magnetic field that is perpendicular to the microwave or RF magnetic field. High power microwave or RF radiation excites the coherent spin precession. Precessing spin-induced induction and absorption signals are picked up by a cavity or a coil and detected by a diode mixer. Although the intrinsic sensitivity is limited by cavity Johnson noise, which is near single-spin detection, this level of detection has never been possible practically. Primary limitations in a conventional experiment are large background noise from high power excitation signal generated by high-power klystron source (need to excite spin in bulk samples) and diode detector noise since a low noise amplifier cannot be employed before a diode detector without being saturated by high level excitation signal pick up at a detection port.

Detailed nano-scale, molecular-level knowledge of the relationships between structure, dynamics, and function of biological macromolecules is a prerequisite for and an integral part of the ability to proceed toward the understanding of the basic principles underlying the regulation of living cells. One major research interest in the biomedical community is how the structure and internal dynamics of proteins lead to biological function. Despite enormous progress in the past decades, there are still major unresolved questions regarding molecular events associated with protein folding. To identify the underlying biochemical processes, magnetic resonance technology has been regarded as an effective probe to determine the structure of proteins. Similar relationships and interests occur in chemistry and materials science.

Spectroscopy and imaging technologies based on magnetic resonance, e.g., electron magnetic resonance (ESR) and nuclear magnetic resonance (NMR) have in the past contributed to fundamental characterization of molecular structure as well as medical diagnosis. Dramatic advances in proteomics and biomedical science have raised challenging demands for nano-scale spatially resolved magnetic resonance spectroscopy and imaging technology with increased sensitivity.

Conventional NMR techniques can determine molecular structure of a large ensemble of homogenous molecules through precise measurement of a chemical shift of nuclear spin resonance in a uniform magnetic field. Non-uniformity of the magnetic field tends to smear out the small chemical shift and reduce, if not eliminate, the effectiveness of a NMR instrument in structure determination. In this situation, NMR machines only have the capability of structural determination for a large volume of homogenous specimen and do not have any spatial resolution.

In contrast, MRI techniques have the capability of imaging with certain spatial resolution (usually in mm range). This capability is realized through a high magnetic field gradient generated in the specimen and the spatial resolution is proportional to the degree of the gradient. The presence of a field gradient smears out chemical shifts and different resonance peaks become one broad peak. Consequently, conventional MRI imaging technique lacks the capability of spectroscopy and structural determination. In the meantime, chemical shifts in nuclear spin resonance also limit the spatial resolution of MRI (10 ppm of typical chemical shift determines that the MRI spatial resolution to be mm).

Figure 3A:
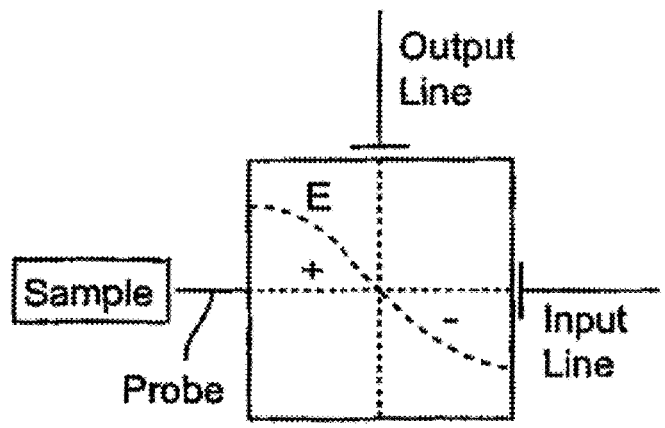
FIGS. 3A and 3B schematically illustrate an orthogonal mode microstrip resonator with a tip to generate an evanescent wave signal and tip shielding structure.
Figure 3B:
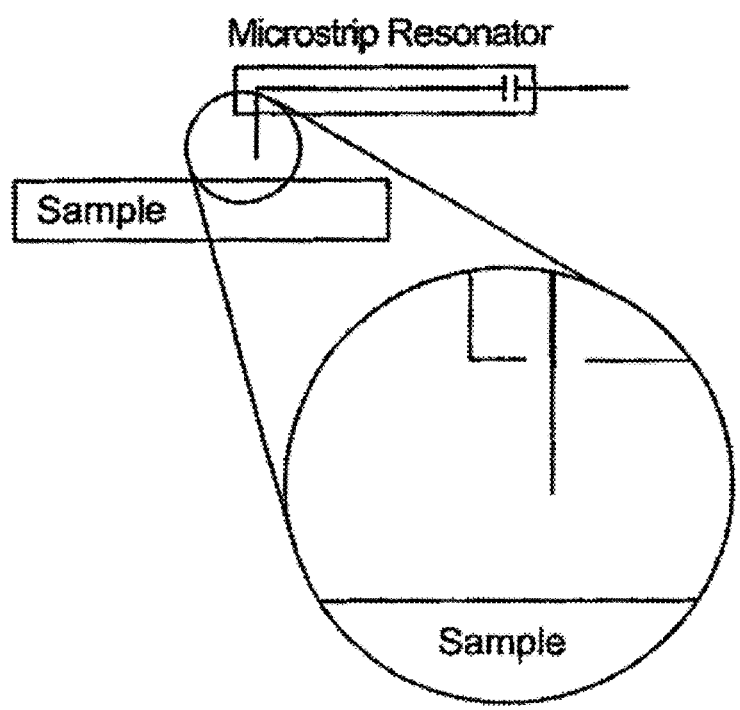

FIGS. 3A and 3B schematically illustrate one exemplary embodiment including a square microstrip resonator or signal coupler, which is open at all four edges, and an associated shield structure for a probe tip. Both input and output transmission lines are coupled to the center of resonator edges with capacitance coupling and at right angle with each other. A probe tip is attached to the opposite side of input line. Because the coupler is square, some of the resonant modes will be degenerate. The electric-field nodal line of one of the pair of lowest-frequency modes is illustrated and the direction of the electric field is shown in the figure. The resonance mode orthogonal to this mode will have a nodal line at horizontal direction. Note that the output microstrip transmission line will not couple to the illustrated mode since the end of the transmission line is an equal-potential surface and is situated symmetrically with respect to the nodal line. Viewed from another perspective, if the described mode is excited, it will not induce any net charge on the end of the output transmission line. However, it will couple to the input transmission line so that power can be fed in from the input line without any power being coupled out to the output line. Optionally, one or more parameters associated with the output line can be adjusted so that, if a sample is not excited, the magnitude of a signal appearing on the output line is minimized (preferably with zero minimum). The square resonator or signal coupler shown in 3A can be replaced by a circular resonator, or by another resonator shape (e.g., a regular octagon) that has at least one set of (two or more) degenerate orthogonal modes.

Figure 4A:
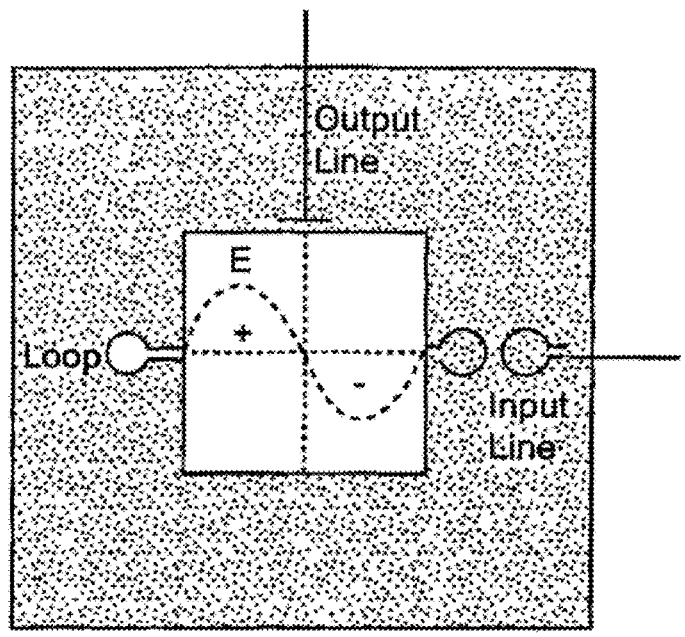
FIGS. 4A and 4B schematically illustrate an orthogonal mode microstrip resonator with loop tip to generate an evanescent wave and an associated shielding structure.
Figure 4B:
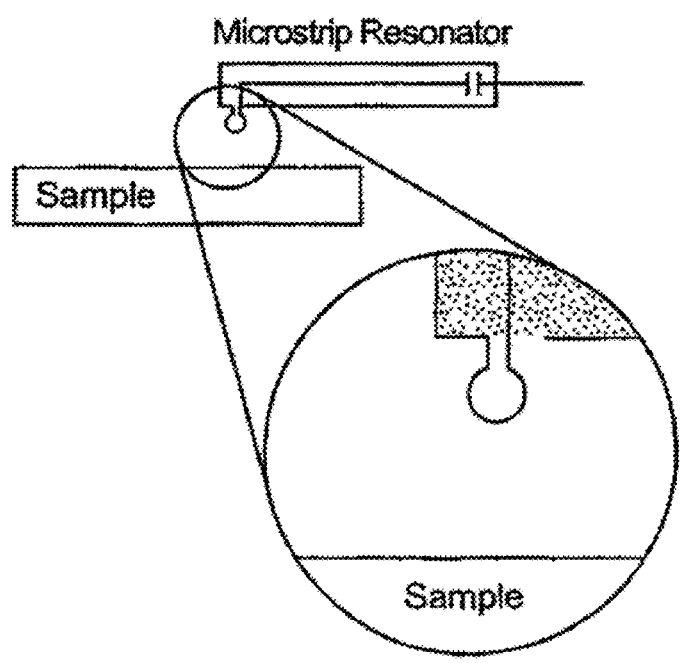

FIG. 4A illustrates a similar orthogonal resonator, where the evanescent wave probe is formed by a small metal loop connected between the center conductor edge and ground plane. When magnetic resonance is excited, this resonance destroys the symmetry of the driving mode, and some power is coupled to the orthogonal mode. As a consequence, the probe or tip will pick up the spin induction or absorption signal, which will be coupled out to the output transmission line and amplified by a low noise RF amplifier. A tip shielding structure for this microstrip resonator is shown in FIG. 4B.

In exemplary embodiments disclosed herein, such as those illustrated in FIGS. 3A, 3B, 4A and 4B, spin resonance of a spin of an atomic constituent can be detected in a time-continuous fashion wherein an excitation magnetic field is applied to a portion of a sample in a time-continuous manner (as opposed to a being applied in a pulsed manner) and wherein the spin resonance is detected using an evanescent wave probe located adjacent to the sample. Such spin-resonance detection is also referred to herein as a time-continuous mode.

Figure 5:
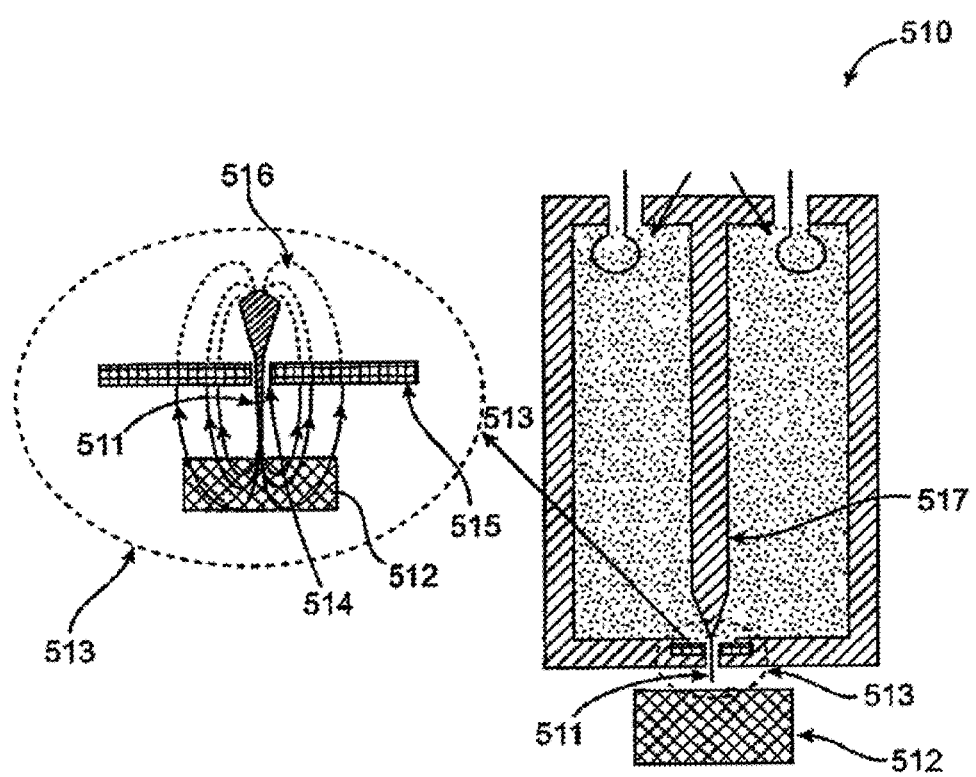
FIG. 5 illustrates the evanescent wave technique in general, showing an exemplary evanescent wave probe (EWP) positioned adjacent to a sample, with electrical field lines emitted from the tip of the probe interacting with the sample.

In time-continuous mode embodiments, two cancellation schemes are available. In an external cancellation scheme, two substantially identical transmission line resonators (either a coaxial line, as shown schematically in FIG. 5 or a microstrip resonator or cavity/waveguide resonator) are used with one equipped with the evanescent probe (tip, loop or aperture as described herein) to generate an evanescent wave and interact with a sample. Optionally, each of two resonators is equipped with an evanescent probe, but only one probe is activated. The essence of the technique relies on creating relatively pure evanescent microwaves near the tip of the probe, while simultaneously maintaining a high quality factor of the microwave sensor (i.e., the resonator). An exemplary EMP system is shown generally at 10 in FIG. 5. One embodiment of the probe's design is based upon a high quality factor (Q) microwave coaxial resonator with a sharpened metal tip 511 mounted on a center conductor 517. Referring to FIG. 5, the region around the tip 511 and sample 512 has been enlarged as a "zoomed in" region 513. The tip 511 extends beyond an aperture 514 formed on a thin metal shielding end-wall 515 of the resonator. Since the tip size is much smaller than the wavelength of the microwave, non-propagating evanescent waves 516 are generated at the tip. Only when the tip 511 is in a close range to the sample 512 will the evanescent waves 16 from the tip interact with the sample materials. Interaction of the evanescent waves with the sample give rise to resonant frequency and Q changes of the cavity, and consequently the microscopy of the electrical impedance.

Figure 6:
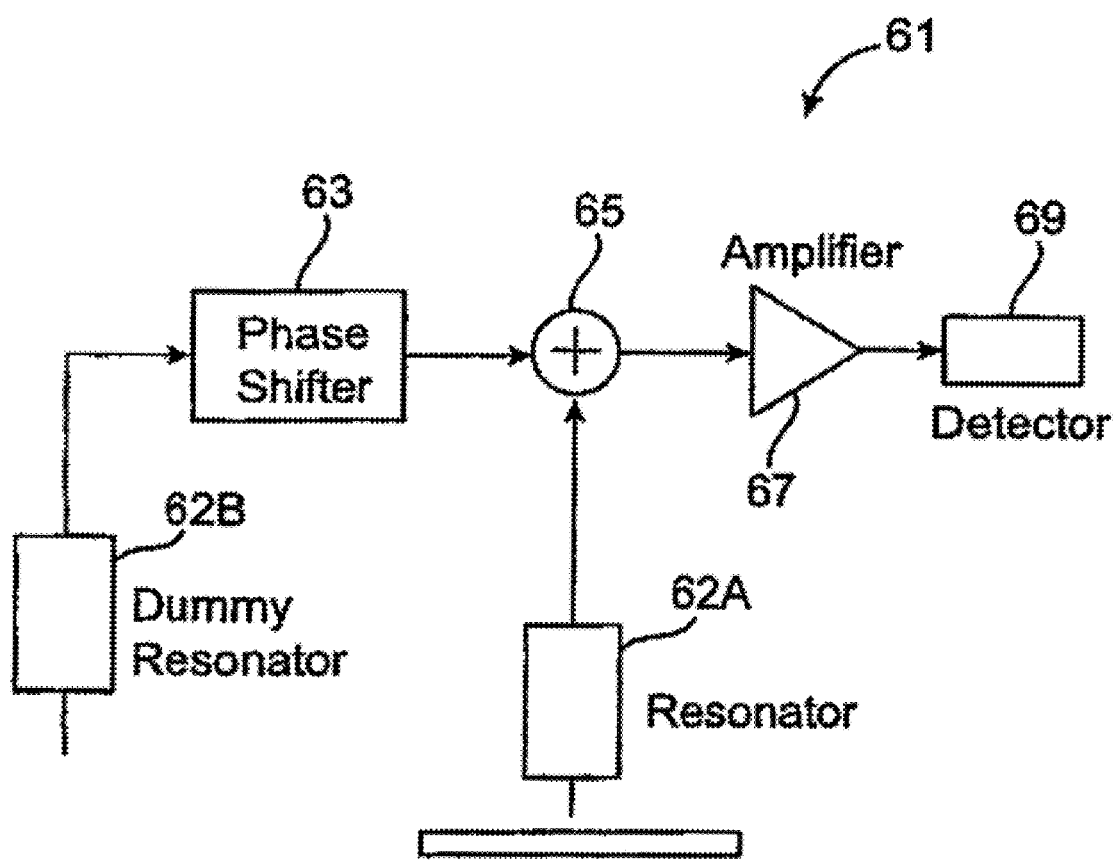
FIG. 6 schematically illustrates an external cancellation approach.

In an external cancellation system 61, illustrated in FIG. 6, first and (phase shifted) second output signals from the first and second resonators, 62A and 62B, are received and processed by a summer or power combiner 65, for background signal cancellation, by an amplifier 67 and by a detector 69.

Figures 7A, 7B:
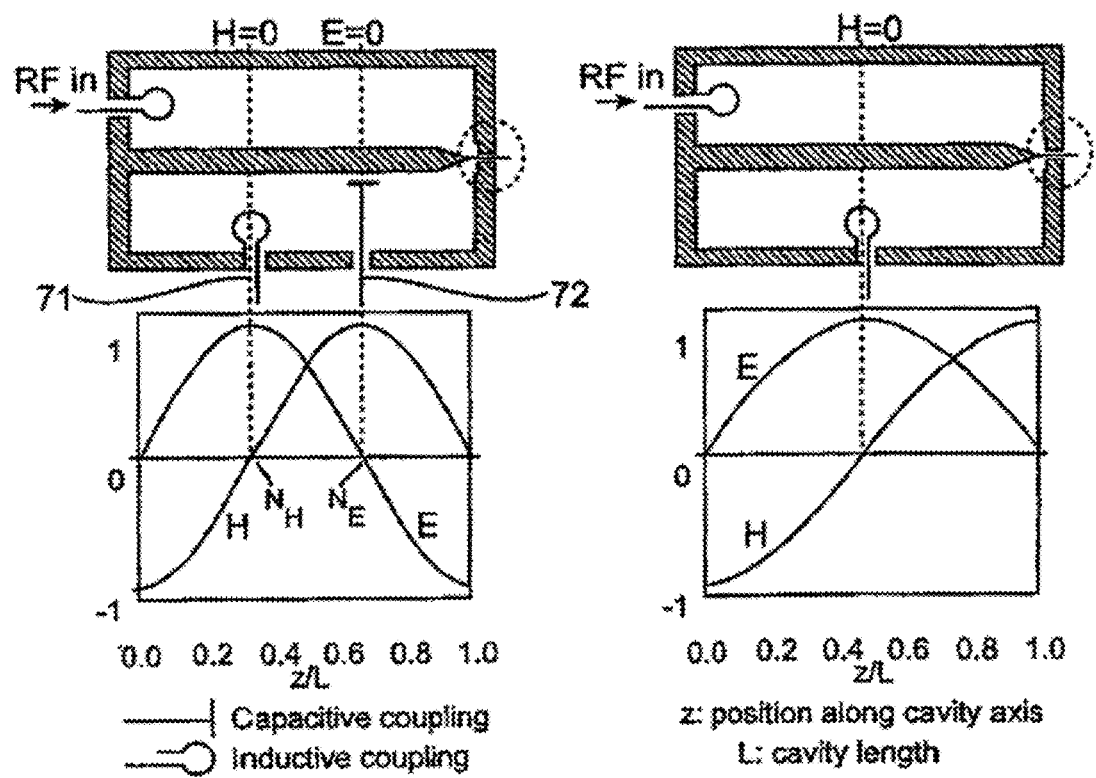
FIGS. 7 and 8 illustrate an internal cancellation scheme (transmission type and cavity type resonator, respectively), where the pickup coupling is positioned at the node of resonance mode of the resonator.
Figure 8:
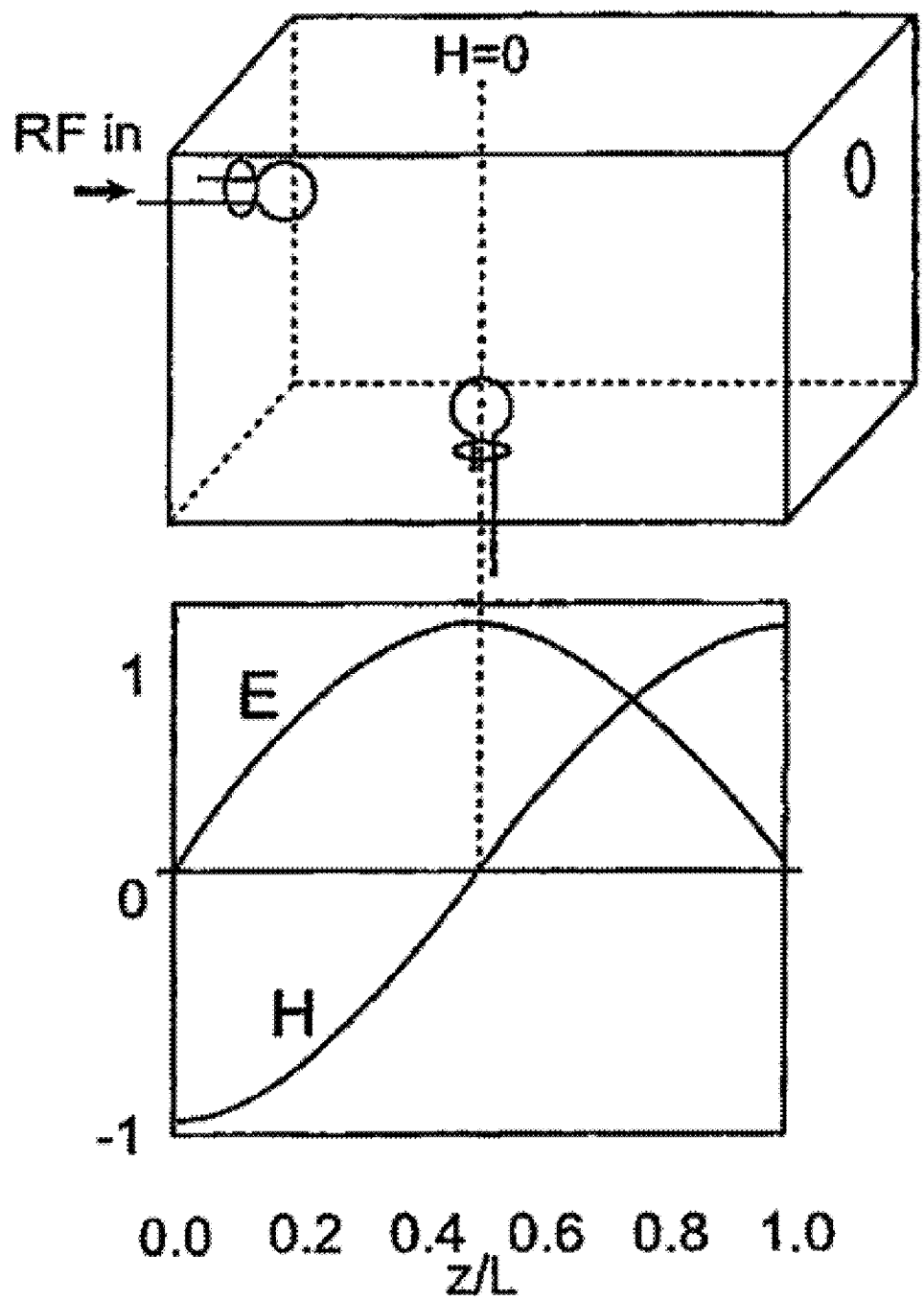

FIGS. 7A, 7B and 8 illustrate the optional internal cancellation schemes (capacitive coupling, inductive coupling and cavity resonator types, respectively) and the corresponding electrical and magnetic fields, where the pickup coupling is positioned at the node of resonance mode of the resonator. As the evanescent probe excites spin resonance, the node condition is broken and pickup coupling then detects the desired spin resonance signal. Here, the probe may be a small aperture in the housing. In the inductive coupling and capacitive coupling modes in FIG. 7A, the magnetic field H and electrical field E, respectively, vanish at the respective housing apertures, 71 and 72.

In another exemplary embodiment, illustrated in FIG. 7A, a node for a resonator or signal coupler is identified, where the signal vanishes or has a very small magnitude for a selected input frequency $f_{in}$ when no sample is present, for example the location marked "N." An output signal pickup module is then located at the node point N, and an input signal with the frequency $f_{in}$ is applied to the coupler to produce an evanescent signal at a sample located adjacent to the probe. A spin resonance response from the sample breaks the symmetry, and a relatively large output signal is then sensed at the node point, representing the spin resonance response of the sample.

Figure 9:
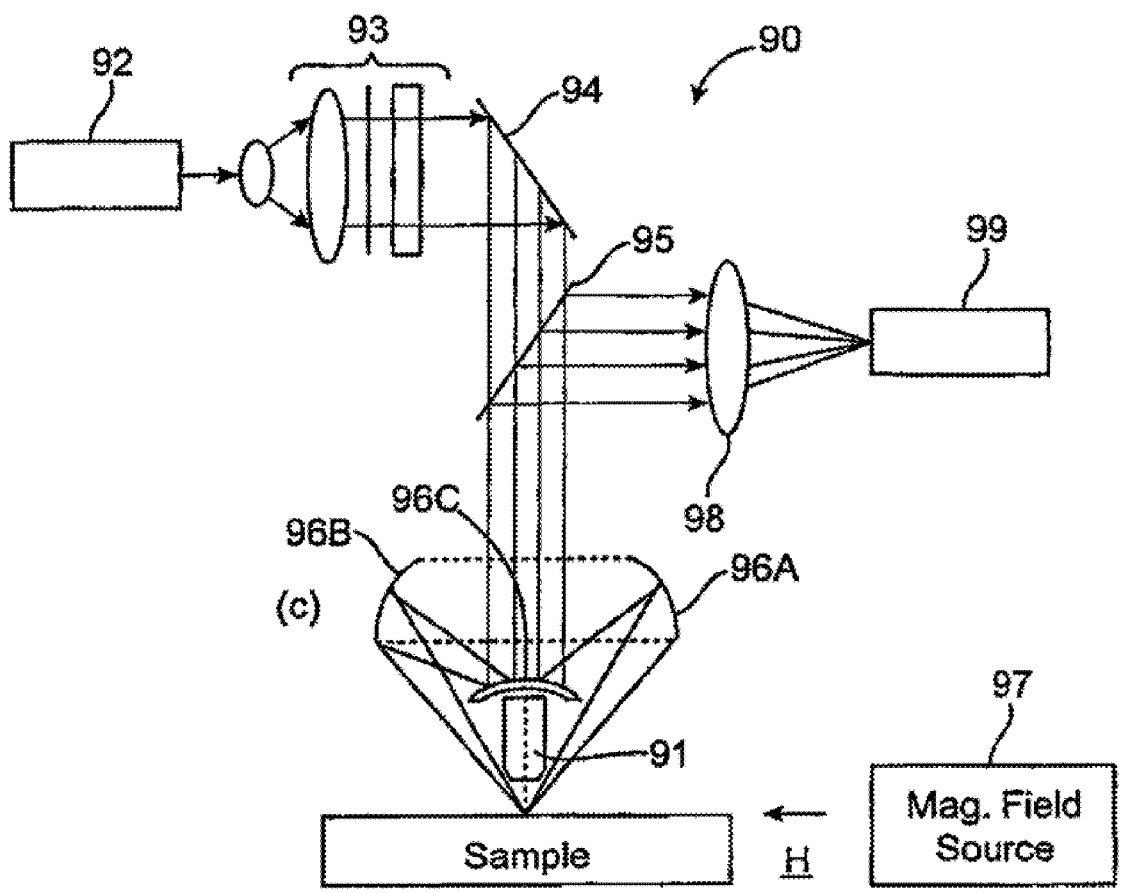
FIG. 9 schematically illustrates an optical pumping system, using a Schwartzschild optical objective, for use with an EMP approach.

In a further exemplary embodiment, fluorescence light is collected with the Schwarzschild optical objective and detected by a photodetector, as illustrated in the system 90 shown in FIG. 9. An evanescent microwave probe (EMP or evanescent wave probe) 91 is used to excite the spin resonance in one version.

A laser beam is generated at a light source 92 and is processed by a first optical system 93, optionally including a lens and/or quarter-wave plate and/or a first linear polarizer. The processed beam is reflected by a first reflector 94, passes through a partly transmissive second reflector 95, and is received by several optical components, 96A, 96B and 96C, of a Schwartzschild objective that directs the laser beam toward the sample. A magnetic field source (dc or slowly swept in field strength) 97 provides a field H that is generally perpendicular to the direction of the EMP signal. Light scattered or generated at the sample is redirected by the Scwartzschild objective components, is mostly reflected by the second reflector 95, is received and processed by a second optical system 98, optionally including a second linear polarizer-analyzer, and is received and analyzed by a detector 99. In a first operating mode, the EMP signal provides sample excitation and the laser beam provides sample interrogation and sensing. In a second operating mode, the roles of the two signals are partly reversed.

By measuring the change of intensity or polarization of fluorescence light produced by the laser beam, one can obtain a spin resonance signal. Optical detection has very high sensitivity, which may allow one to achieve single spin detection. In order to achieve this high sensitivity, the cancellation of transmitted pumping light background is necessary. Transmitted light is usually circularly polarized, while the fluorescence light is usually linear polarized. A quarter-wave plate can be used to transform the circularly polarized transmitted light to linear polarized light, which is oriented at a right angle to the polarized direction of fluorescence light. In this case, a linear polarizer can be used to block the transmitted light and allow the fluorescence light to pass.

In a transmission type resonator with an evanescent wave probe, a shielding wall with an aperture, from which the probe (metal tip or loop) extends from the resonator and interacts with the sample, can be used to increase the spatial resolution.

Figure 10:
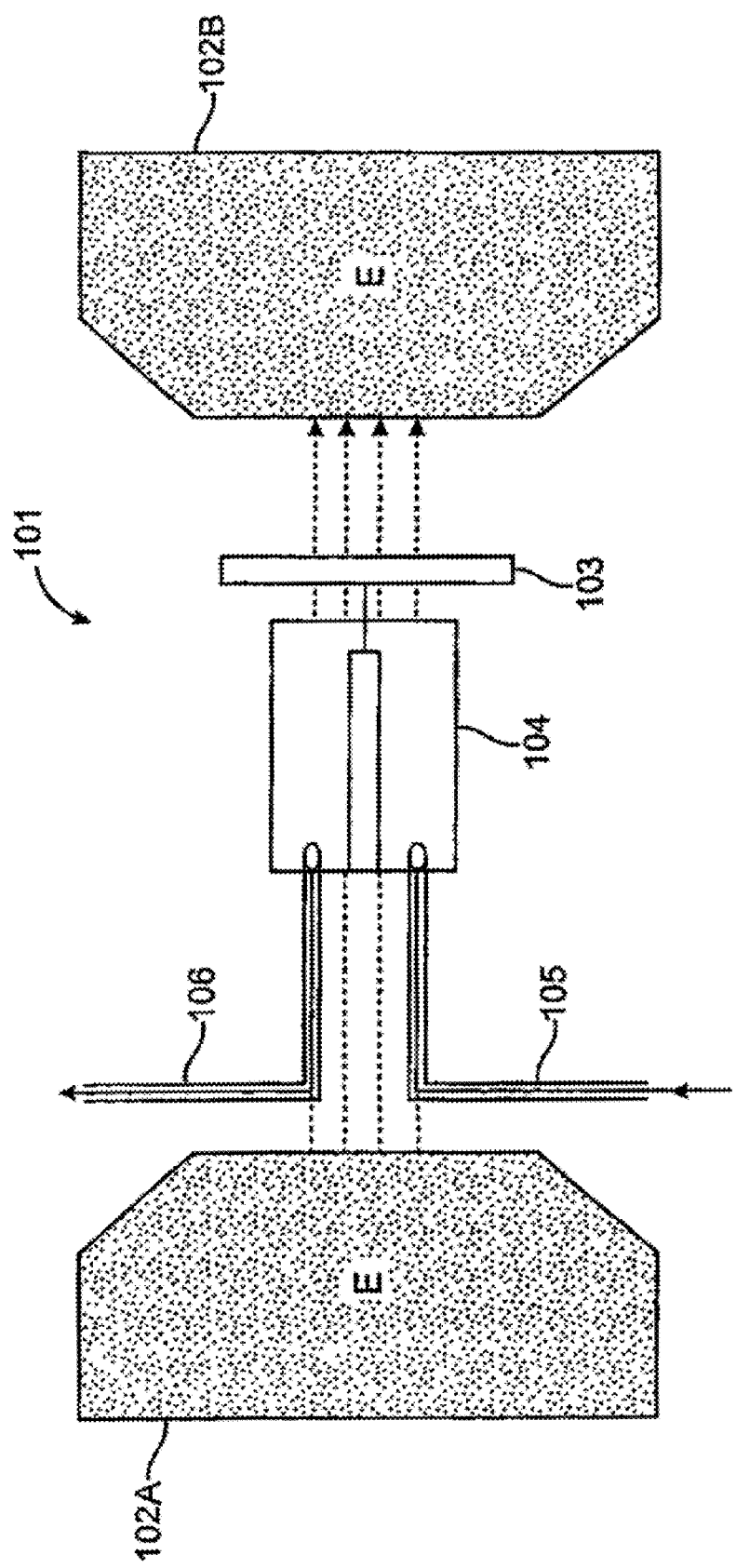
FIG. 10 schematically illustrates use of EMP apparatus for magnetic resonance detection.

An embodiment of an experimental set-up 101 is illustrated in FIG. 10. Two spaced apart electromagnet poles, 102A and 102B, have a sample 103 positioned between them. An EMP probe 104, located adjacent to the sample 103, is fed by an RF signal source 105 and transmits evanescent waves to the sample. Spin resonance signals are detected by the EMP probe 104 and are transmitted by an RF signal output module to a suitable detector-analyzer.

A measurement of ferromagnetic resonance (FMR) of a YIG single crystal was conducted using an Evanescent Microwave Probe. The sample is a YIG single-crystal with a dimension of 4 mm×4 mm×0.5 mm. The electromagnet has a 1.5" gap between a pair of 3" diameter poles. The shape of the poles was designed to have a magnetic field uniformity of about $10^{-5}$ in a 1 cubic inch sample volume at the center of the gap.

In the FIG. 10 example, the measurements were made by attaching the sample to an EMP tip. The EMP resonator serves as a spin resonance excitation RF source as well as a detector. EMP microwave electronic and digital acquisition system measures the changes in cavity resonant frequency and quality factor Q while scanning the external magnetic field. When a ferromagnetic resonance condition is satisfied, a sample volume near the EMP tip will interact with EMP. This condition was detected by measuring resonant frequency $f_r$ and quality factor Q of the EMP resonator.

The EMP can be made of a $\lambda/4$ transmission line resonator, as illustrated in FIG. 5 (a coaxial resonator or a microstrip resonator are two examples) with an electrically conducting tip connected to the central conductor or a loop connected between the center conductor and ground shielding, or cavity type resonator with an aperture type evanescent probe. To achieve better spatial resolution, the end-wall of the resonator can be shielded by a thin metal film with an aperture in transmission type resonator cases. A tip or loop for the probe extends beyond the shielding wall from the aperture. An EMP tip is used to provide microwave radiation and define the spatial resolution.

A variety of evanescent wave probes (also called herein EWP) can be included in the spatially resolved spin resonance spectroscopy systems, apparatus, and methods disclosed herein. For example, the evanescent wave probe can be an evanescent microwave probe (also called herein EMP) or any other type of evanescent wave probe operating in a different wavelength region, e.g., radio frequencies (RF). Various embodiments disclosed herein are described as using an EMP, but it should be understood that an evanescent wave probe of any frequency can be used. Some of the example evanescent wave probes are shown in FIGS. 7A to 7B and FIGS. 11 to 14B.

Figure 11:
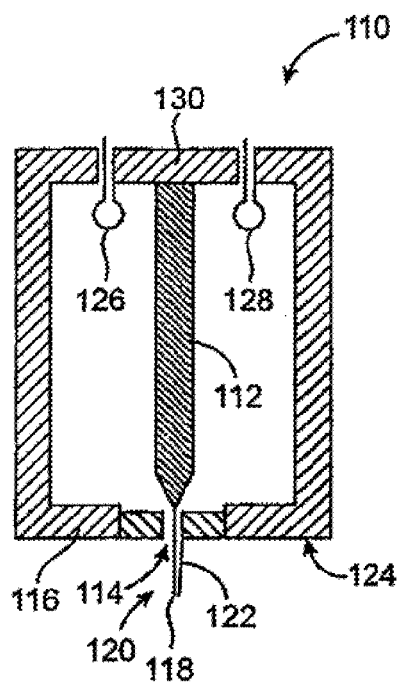
FIGS. 11 to 13 illustrate various exemplary embodiments of an evanescent wave probe.

FIG. 11 schematically illustrates an evanescent wave probe 110. A center conductor 112 extends at a distal end beyond a small aperture 114 in the shielding end-wall 116 and forms a tip 118. Depending on the length of the outside portion 120 of the tip 118, the oscillating current flowing along the tip 118 will produce RF radiation to a scale much larger than the size of tip 118, which will decrease the EMP space resolution. To reduce the far-field radiation effect, a grounded metal wire 122 is connected to the cavity shielding 124 and placed adjacent to the center conductor 112 at the outside portion 120 of the tip 118. The construction of the evanescent wave probe 110 limits the electromagnetic field effectively between the tip 118 and the ground wire 122 and increases the space resolution dramatically. The evanescent wave probe 110 also optionally includes a first loop 126 on an end-wall and a second loop 128 on an end-wall. The end-wall can be any end-wall, such as second end-wall 130 opposite end-wall 116. The first loop 126 and second loop 128 can each, independently and optionally, be connected to a source for electromagnetic energy, such as a RF generator (shown in FIG. 16), or a detector for electromagnetic energy, such as a RF detector (shown in FIGS. 16 and 17). The loop 126 and 128 (and corresponding features illustrated in FIGS. 12 and 13) provide for inductive coupling of electromagnetic radiation, e.g., RF, Microwave and other, into and out of the evanescent wave probe 110. Optional, one or more of the loops 126 and 128 can be replaced with capacitive elements or with direct electrical connections to capacatively or directly couple electromagnetic radiation into and out of the evanescent wave probe 110.

When only connected to a detector for electromagnetic energy, the evanescent wave probe 110 operates in a passive mode to detect a signal. When connected to a source for electromagnetic energy, the evanescent wave probe 110 operates in an active mode to further generate an evanescent wave.

Figure 12:
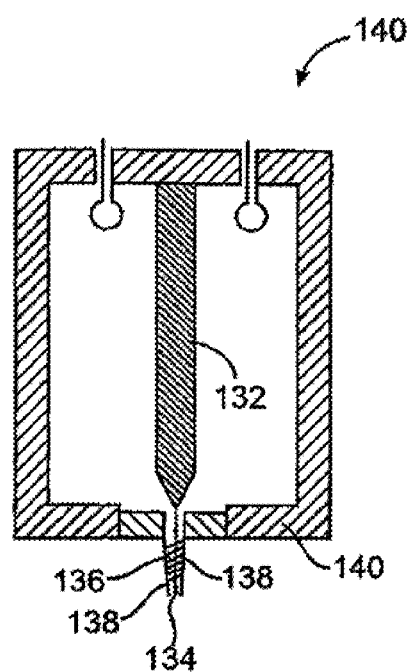

Similar to the structure in FIG. 11, FIG. 12 schematically illustrates an evanescent wave probe 140. In this exemplary embodiment, instead of a grounded wire, the outside part of the tip 134 of the center conductor 132 is surrounded by low loss insulating material 136, and then coated with a layer of conductive film 138, which is electrically connected with the cavity shielding at, for example, end-wall 140. The illustrated structure in FIG. 12 substantially eliminates the far-field RF radiation and has better resolution than a two wire structure.

Figure 13:
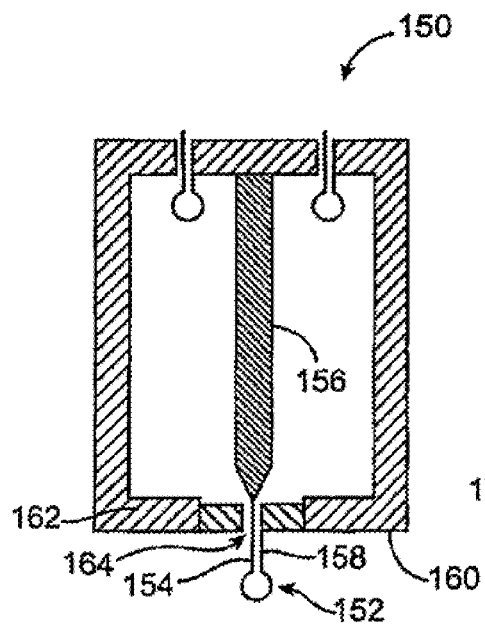

The tip of the evanescent wave probe cavity can optionally be replaced with a conductive loop 152 as shown in the exemplary embodiment 150 of FIG. 13. One side 154 of the conductive loop 152 is connected to the center conductor 156 and another side 158 is connected to the cavity shielding 160, at, for example, end-wall 162. The conductive loop 152 extends beyond an aperture 164. The aperture can be at a thinned metal shielding portion of end-wall 162 and connects back to the end-wall 162 to form a λ/2 resonator.

In exemplary embodiments, the conductive loop 152 can be either a single-loop structure or a multiple-loop coil. Also, the evanescent wave probe can be used for NMR/ESR signal excitation and detection. The oscillating magnetic field inside the sample produced by the one or more conductive loops is in a horizontal direction, which is perpendicular with the external static magnetic field.

Because the current flowing in the two wires connecting the loop is in opposite direction with each other, the RF radiation emitted by these two wires will effectively cancel each other to a very low level. Thus, only the portion of the sample immediately under the loop will be sensed. Compared to the tip structure in FIGS. 11 and 12, the loop probe in FIG. 13 is much more sensitive to magnetic signal, but has a lower resolution.

Figures 14A, 14B:
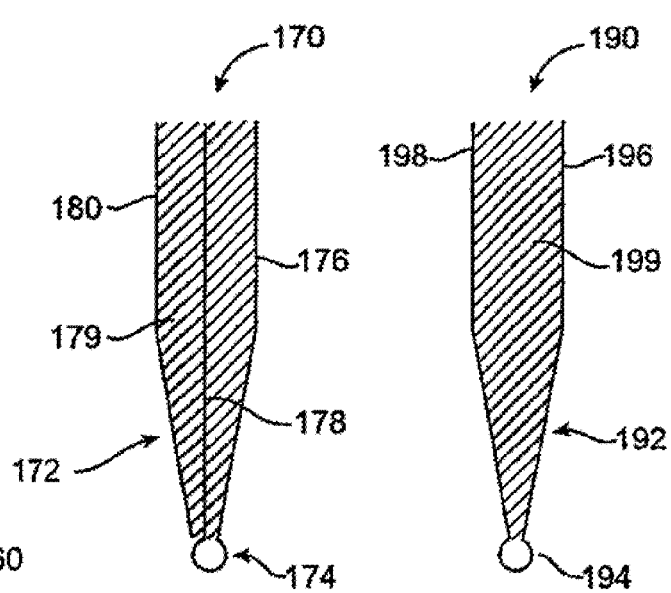
FIGS. 14A and 14B illustrate two exemplary embodiments of a transmission line type evanescent wave probe.

The schematically illustrated exemplary loop structure can also be used in transmission line type probes, such as the exemplary transmission line 170 illustrated in FIG. 14A or transmission line 190 illustrated in FIG. 14B. The transmission lines 170, 190 include two conductive lines 176, 178 and 196, 198. Optionally, a dielectric insulating material 179, 199 can be placed between and/or around such conductive lines. Transmission line 170 can also include a further shield electrode 180 connected, for example, to ground. The front end 172, 192 of the transmission line 170, 190 is optionally tapered down to increase spatial resolution, and a conductive loop 174, 194 is attached thereto. The tapered region of the transmission line is at a distal end of the structure, such as a distal end from a housing, a mounting surface, a control surface, or a clamping structure supporting and/or manipulating the transmission line. In one exemplary embodiment, the transmission line is substantially configured as a coaxial cable. For coaxial cable, the loop is connected to the center conductor and outside shielding layer. For the structure in FIG. 14B, the loop is connected to the two conductive lines. The examples illustrated in FIGS. 14A and 14B each include two conductive lines 170A, 170B and 190A, 190B. However, multiple pairs of conductive lines can be used in each exemplary embodiment, e.g., four conductive lines in each exemplary embodiment, each pair of lines optionally having a conductive loop. Optionally, the transmission line type probe with a tapered region of the transmission line may be positioned at a distal end of the structure may not include a conductive loop at the end of the tip.

Figure 15A:
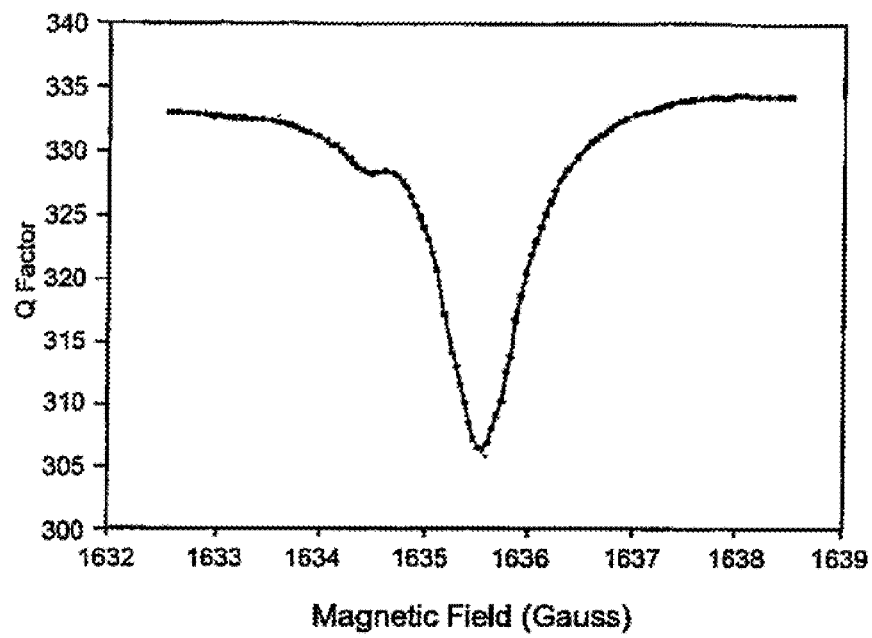
FIGS. 15A and 15B graphically EMP resonance and Q factor versus magnetic field strength H for a YIG sample.
Figure 15B:
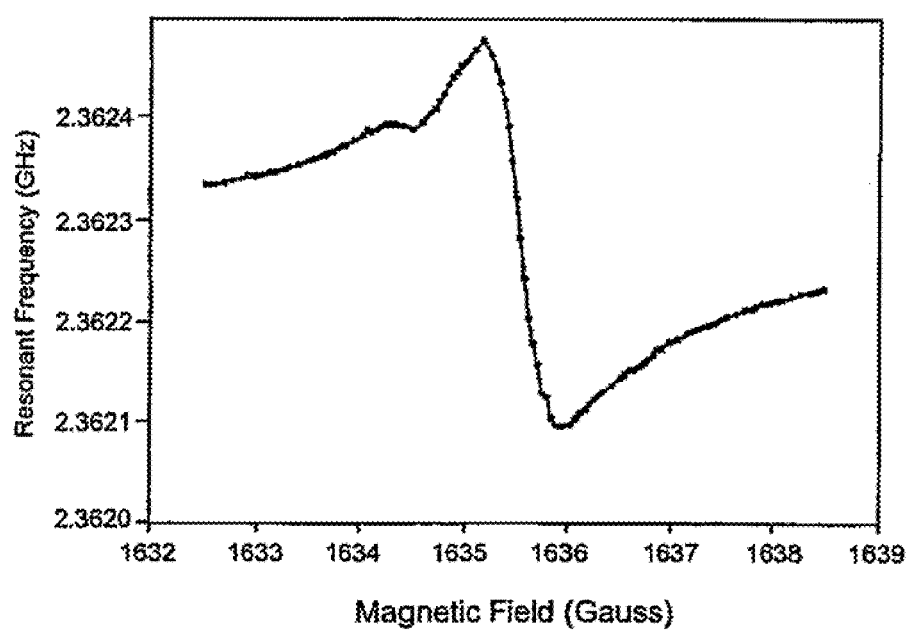

FIGS. 15A and 15B graphically illustrate FMR curves obtained by measuring the EMP resonant frequency and Q versus external magnetic field H using an evanescent wave probe. The relation between $f_r$ and H arises from changes in the propagation constant of the probe circuit that are caused by a dispersion influence of the real part of the permeability $\mu'$, according to a relation $$\mu' = 1 + \frac{\gamma 4\pi M(f - f_0)}{(f^2 - f_0^2) + \gamma^2(\Delta H)^2} \quad (2)$$

$$\approx 1 + \frac{\gamma 4\pi M(f - f_0)}{\gamma^2(\Delta H)^2} \text{(near resonance)}$$

where $f_0$ is the FMR frequency and $\gamma$ (=2.8 GHz/kOe) is the gyromagnetic constant. Absorption of microwave energy will reduce the Q factor of the probe through the resonance peak in the imaginary component $\mu''$, according to $$\mu'' = \frac{\gamma 4\pi M \gamma(\Delta H)}{(f^2 - f_0^2) + \gamma^2(\Delta H)^2} \quad (3)$$

$$\approx \frac{\gamma 4\pi M}{\gamma(\Delta H)} \text{(at resonance)}$$

The actual FMR condition is established when the proper Kittel relation is satisfied. In this experimental configuration, $$f_0 = \gamma\sqrt{H(H+H_K+4\pi M)}, \quad (4)$$

where $H_K$ is the anisotropy field ($\approx$50 Oe) that is usually ignored when approximate values are sufficient.

Where ferromagnetic spin resonance is of interest, the invention provides a direct readout of real and imaginary parts of the RF permeability for extremely small specimen volumes of ferro- or ferrimagnetic materials. A line width associated with ferromagnetic resonance response (FMR) of a single crystal of yttrium-iron garnet (YIG), illustrated graphically in FIG. 15A, approaches the practical limit of less than 1 Oe at room temperature for commercially available chemical purity and crystal perfection. YIG and similar ferrimagnetic and ferromagnetic compounds can be used to "tag" a suitable target compound in order to more easily sense the presence or condition of the target compound.

In another embodiment, high spatial resolution, high contrast topography and high sensitivity spin magnetic resonance spectroscopy are simultaneously achieved using a pulsed NMR technique with an evanescent microwave probe (EMP), integrated with an atomic force detection sensor.

An evanescent microwave probe (EMP), a highly sensitive microwave detection technology as previously described and illustrated herein, operates by sending evanescent microwave and detecting its interaction with the sample through a conducting tip. Evanescent wave differs from the far-field wave in that it does not radiate or propagate in space, but is localized only near the surface of a sharp conducting tip. Evanescent wave has a much higher spatial resolution than the propagating microwaves or RF waves (~$\lambda$).

The conducting tip has a radius much less than the microwave wavelength ($\lambda$) connected to a microwave resonator. This interaction depends on complex electrical impedance (including both the real and the imaginary parts) of the sample. The interaction causes a change in resonant frequency ($f_r$) and quality factor (Q) of the resonator. The EMP can simultaneously measure the real and imaginary part of the sample's electrical impedance as well as the surface topography by detecting the shift in resonance frequency and quality factor of the sensing resonant probe The EMP obtains relatively pure evanescent microwave near the tip while at the same time maintaining a very high quality factor (Q) of the microwave sensor (resonator). The probe is based on a high Q resonator, e.g., microwave coaxial resonator, with a sharpened metal tip mounted on a center conductor. Since the tip is an integral part of a sensitive detector (microwave resonator with Q of a few thousands), the sensitivity of the instrument can be very high. The tip extends beyond an aperture formed on a thin metal shielding end-wall of the resonator. The tip and the shielding structure are designed so that the propagating far-field components are shielded within the cavity whereas the non-propagating evanescent waves are generated at the tip. Only when the tip is in close proximity of the sample will the evanescent waves on the tip interact with the materials. Both theoretical and experimental analysis indicate that the EMP tip picks up signals from a small volume proportional to (tip radius)³. Sub-micron spatial resolution has been realized with tip radius on the order of one micron.

Conventional NMR/ESR measurements suffer limited spin sensitivity due to a large power signal background, which will decrease the instrument's ultimate sensitivity dramatically. To reach the intrinsic sensitivity, the background signal should be decreased to as low as possible without sacrificing the excitation power. To move toward a zero background limit, a pulsed detection configuration (e.g., a time-resolved detection configuration) can be utilized in exemplary embodiments. The basic idea of the pulsed technique is to apply a certain time of RF excitation signal to the sample, and to detect the emitted RF signal from the sample after the pulse. Since the detection and excitation do not occur at the same time, there is no background power coupling from the excitation signal. What is detected comes substantially purely from the spin resonance of the sample. Therefore, a true zero background signal detection limit can be approached and the intrinsic high sensitivity achieved.

Figure 16:
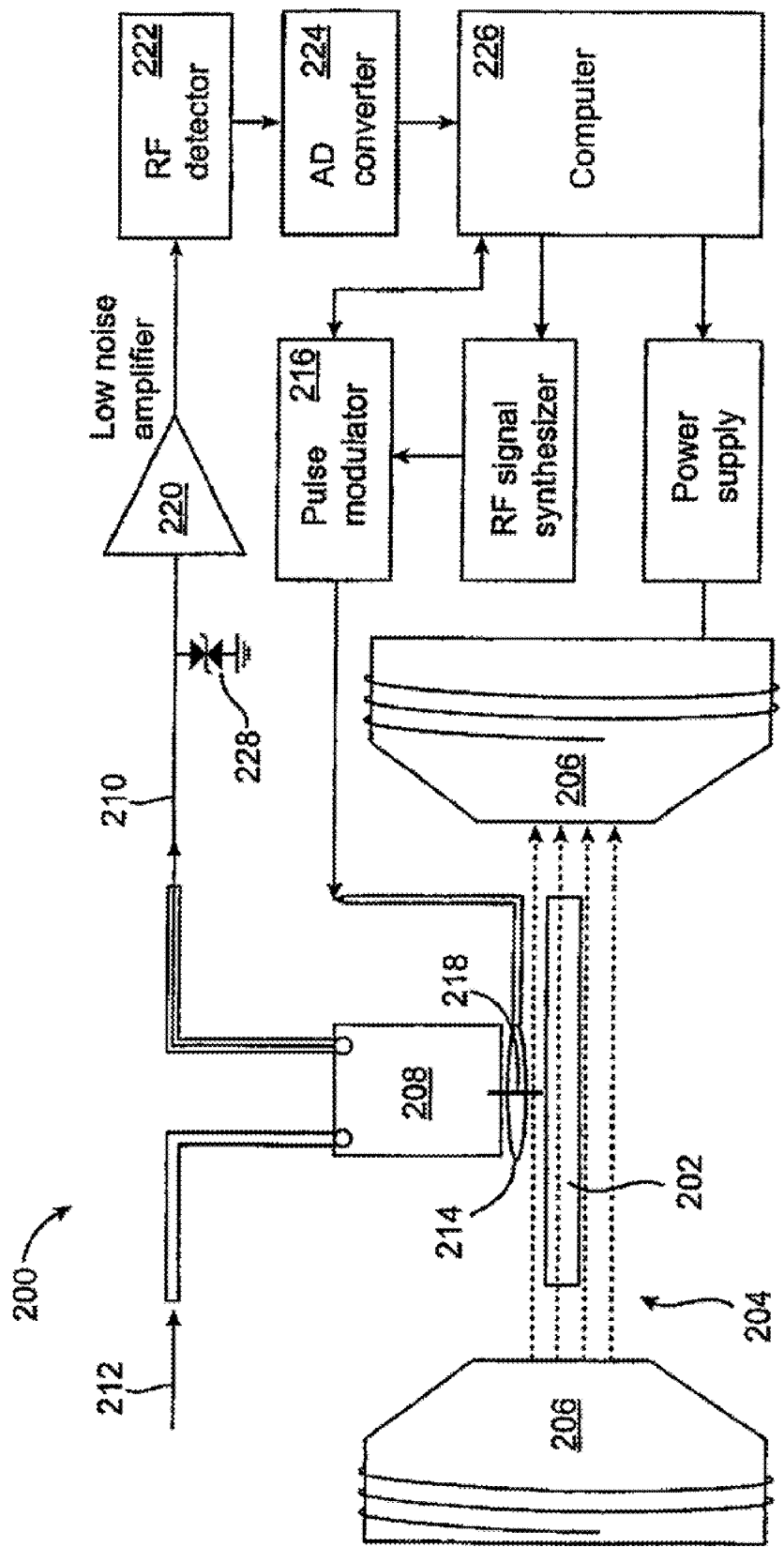
FIG. 16 is a schematic illustration of an exemplary embodiment of an apparatus for spatially resolved spin resonance spectroscopy.

In one exemplary device configuration 200 illustrated in FIG. 16, the sample (with scanning stage 202) is placed in a uniform magnetic field 204 generated by electromagnet 206. A RF resonator 208 (such as a helical resonator for NMR measurement or a coaxial resonator for ESR measurement) can be used as a passive sensor to detect spin resonance (corresponding to output signal 210), in which case a small orthogonal RF coil 214 is controlled by the pulse modulator 216 to apply an intense RF excitation pulse to the sample. Optionally, the RF resonator 208 can be used as an active sensor by supplying excitation energy 212 to the RF resonator 208 to excite the sample, the RF resonator 208 also being used as the spin-resonance sensor. The RF resonator 208 is placed just above the RF coil 214 with its metal tip 218, e.g., a distal end of a tip of an evanescent wave probe, going through the RF coil 214 center. The frequency of the RF excitation signal will be tuned to the same or close to (e.g., within a bandwidth) of the resonant frequency of the RF resonator 208. For simplicity, the quartz tuning fork mounted on the RF resonator is not drawn here.

Typical experiments begin with the net nuclear spin magnetization $\overline{M}$ aligned along the magnetic field direction. During measurement, a certain width of the RF pulse will be applied to the sample under the RF coil so that the nuclear (or electron) spins of the sample will rotate 90° from their original direction and align in a direction perpendicular to the magnetic field. The magnitude of the applied RF magnetic field $H_1$ and the applied pulse time width $t_w$ have to satisfy the following relationship to achieve the 90° spin rotation, $$\gamma H_1 t_w = \frac{\pi}{2}, \qquad (5)$$

where $\gamma$ is the gyromagnetic ratio of nuclear (or electron) spin.

After cessation of the pulse, the 90° bended spins will start to precess around the axis of magnetic field direction. This precessing induced RF emission will be picked up by the RF resonator 208 through tip coupling, amplified by a low noise RF amplifier 220 and finally detected by a RF detector 222. The detected signal will be converted to a digital signal by an AD converter 224 and processed by a computer 226. A Zener diode 228 is used in front of the low noise amplifier 222 to limit the input RF power caused by the RF pulse and for protection.

In the exemplary embodiment illustrated in FIG. 16, a time-resolved and spatially resolved measurement of impedance in a sample can also be made, either alone or in conjunction with a spin-resonance measurement as discussed above. In such a time-resolved impedance measurement, the RF resonator 208, or any suitable evanescent wave probe as described herein, is positioned adjacent to a sample. Such an evanescent wave probe is configured to generate an evanescent wave including at least one of a time varying amplitude and a time varying phase. A detection circuit, such as RF detector 222, detects a time-resolved change in a resonance frequency of the evanescent wave probe and a time-resolved change in a quality factor of the evanescent wave probe. A processing system, such as computer 226, processes the change in the resonance frequency and the change in a quality factor to produce an impedance measurement using suitable algorithms, such as described in U.S. Pat. Nos. 5,821,410 and 6,532,806, the entire contents of which are incorporated herein by reference.

Figure 17:
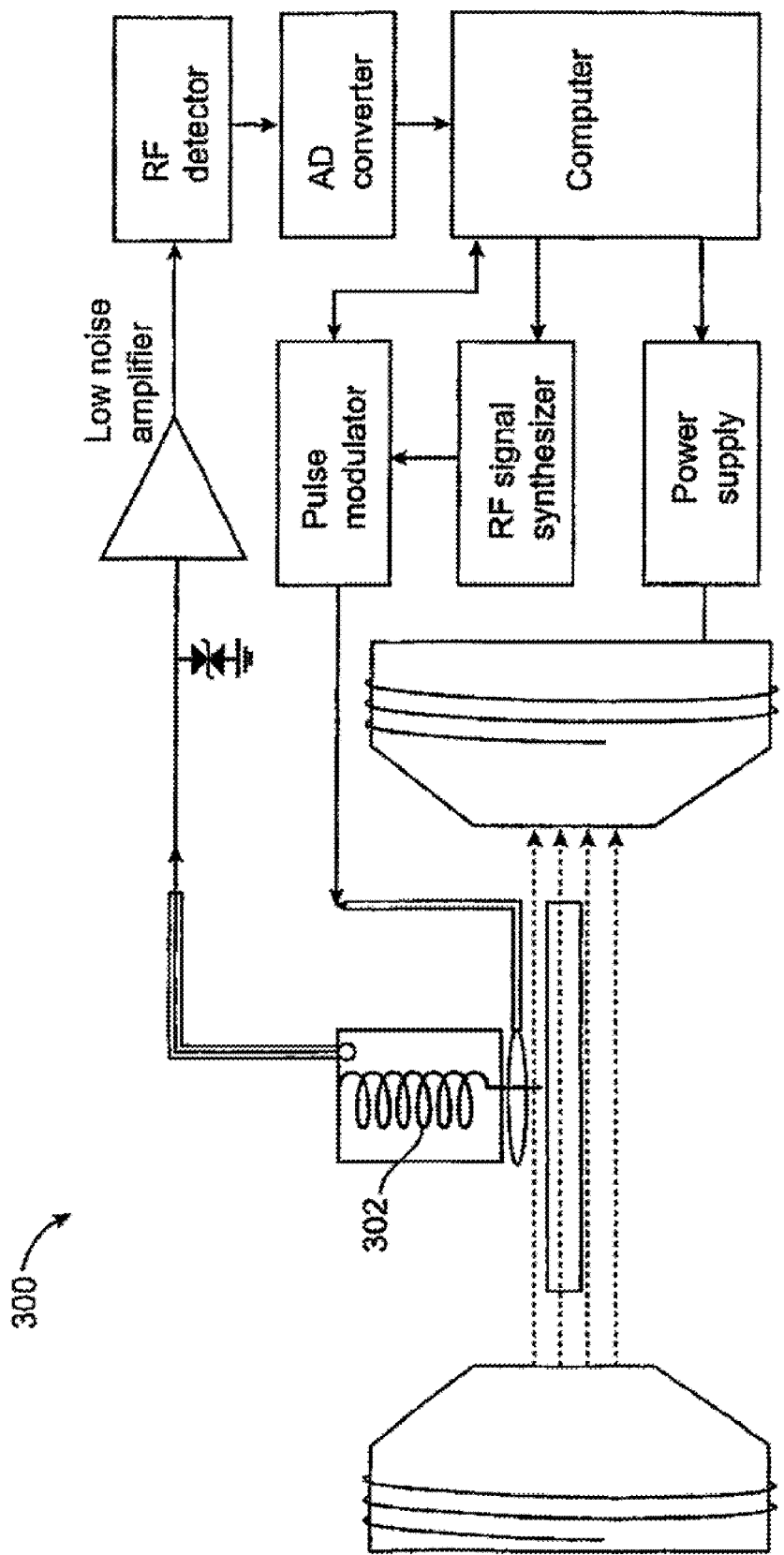
FIG. 17 is a schematic illustration of another exemplary embodiment of an apparatus for spatially resolved spin resonance spectroscopy where the evanescent wave probe includes a helical coil.

FIG. 17 is a schematic illustration of another exemplary embodiment of an apparatus for spatially resolved spin resonance spectroscopy where the evanescent wave probe includes a helical coil. The FIG. 17 exemplary embodiment 300 is similar to the embodiment 200 described with respect to FIG. 16. In FIG. 17, the RF resonator is illustrated with a helical coil 302. Also, the embodiment 300 is illustrated as an optional passive device because no input, analogous to input 212 of FIG. 16, is supplied to the RF resonator.

In addition to a time-continuous mode of spin-resonance detection, such as described above, exemplary embodiments can employ a time-resolved mode of spin-resonance detection such as when a pulse of magnetic energy is applied to a portion of a sample, and a spin-resonance measurement is made subsequent to the pulse.

In a time-resolved mode of detection, a time-resolved measurement of at least one property of the spin resonance can be made using the evanescent wave probe (or other type of probe such as described herein). Exemplary properties include a resonant frequency and a time decay, e.g., a relaxation time. In a time-resolved mode, a detected spin processing signal will start to decay after an applied pulse is removed/completed due to the spin-spin and spin-lattice interaction inside the sample. This is the spin relaxation time. Due to near field effect, the RF resonator tip 218 only picks up the emitted signal coming from a very small volume of the sample in the proximity of the tip 218, which has a dimension of about 1 mm$^3$ to 10$^3$ nm$^3$. By scanning the sample, a high spatial resolution spin resonance image of the sample can be obtained.

The image contrast comes from the different intensity or line width of spin resonances, or chemical shift of the nucleus in sample molecules. For NMR, chemical shift actually means the spin resonance frequency difference between different nucleus or different molecules in different locations. When the experiment is operated in one fixed RF frequency, some parts of a sample will have spin resonance and some parts will not have spin resonance or will have a weak spin resonance because of the chemical shift. As a result of this difference, a difference or contrast will appear in the detected spin resonance data.

In addition, in time-resolved mode the evanescent wave probe can be replaced in the exemplary embodiments disclosed herein by a miniature magnetic sensor to conduct time-resolved NMR. The miniature magnetic sensor can be any suitable magnetic sensor sized to sense a sample volume having an order of magnitude of about 1 mm$^3$ to 10$^3$ nm$^3$. Examples of minicoils and microcoils suitable for adaptation for use as the miniature magnetic sensor are disclosed in U.S. Pat. No. 6,097,188, the entire contents of which are incorporated herein by reference.

Figure 18:
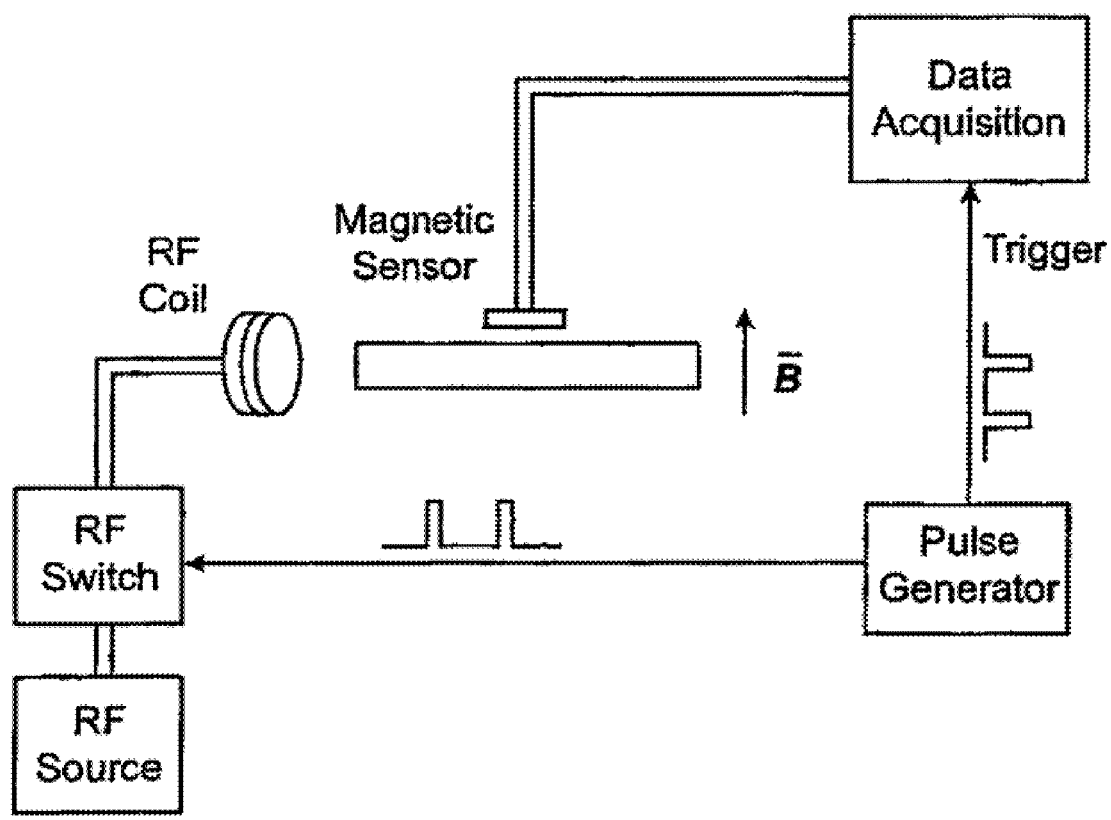
FIG. 18 is a schematic illustration of another exemplary embodiment for spatially resolved spin resonance spectroscopy using a miniature magnetic sensor.

Various other kinds of magnetic sensors, such as tunneling magnetoresistance sensors (TMR), giant magnetoresistance sensors (GMR), Hall devices, or magneto-restrictive sensors, can also be used as a miniature magnetic sensor, instead of an evanescent wave probe, for carrying out time-resolved spin-resonance detection as described herein. As illustrated in FIG. 18, a miniature magnetic sensor is used to detect the magnetic signal induced by spin resonance, while a RF coil is placed close to the sample to provide RF excitation signal. The oscillating magnetic field produced by the RF coil is perpendicular to the external magnetic field $\vec{B}$.

The real part of the susceptibility near spin resonance has the following relationship with RF frequency ω (or magnetic field H), $$\mu' = 1 + \frac{\gamma 4\pi M(\omega - \omega_0)}{(\omega^2 - \omega_0^2) + \gamma^2(\Delta H)^2} \quad (6)$$

$$\approx 1 + \frac{\gamma 4\pi M(\omega - \omega_0)}{\gamma^2(\Delta H)^2} \text{ (near resonance)}$$

By measuring the susceptibility of the sample, magnetic sensor can be used to detect spin resonance. The time-resolved measurement is achieved by modulating the RF coil signal with a RF switch and a pulse generator, and in the mean time, measuring the spin resonance signal decay with pulse synchronized data acquisition.

In further exemplary embodiments, independent tip-sample distance control can be integrated into any of the exemplary embodiments disclosed herein, e.g., the spin resonance system and/or the impedance system, for magnetic resonance detection. For example, tip-sample distance control can be provided by a scanning probe microscope (SPM). The sensitivity of SPM is a function of tip-sample distance. Since the EMP tip will sense the magnetic resonance induced induction and absorption, a known tip-sample distance during magnetic resonance detection contributes to precise interpretation of the detected signal. Additionally, when a highly conductive sample is measured tip contact with the surface greatly reduces the Q, which determines the sensitivity.

In one exemplary embodiment, SPM in the form of atomic force microscopy (AFM) is integrated with the spin resonance and/or impedance systems to control probe sample distance. The EMP can utilize such control to realize its powerful capacities for microwave impedance detection.

Atomic force is known to have strong dependence on tip-sample distance and has been widely used to image surface topology of various samples. Exemplary embodiments integrate a commercial quartz tuning fork cantilever with the EMP system as a tip-sample distance control mechanism by detecting the atomic force between the tip and the sample. The quartz tuning fork base is fixed rigidly on the resonator cavity, and the EMP tip is attached to one of the tuning fork arms using an adhesive. During measurement, the tuning fork is driven by an AC signal synthesizer with a frequency the same as or close to the resonant frequency of the tuning fork. The tuning fork's vibration signal is read by using a detection circuit. The variation of atomic force between the EMP tip and measured sample (i.e., the tip-sample distance change) will dramatically change the resonant frequency and quality factor of the tuning fork. Therefore, the tuning fork signal can be used to measure the sample's topography and to regulate the EMP tip-sample distance.

There are many ways to realize the atomic force detection, some of which are summarized in Table 1. There are basically three atomic force modes, one is a DC mode and two are AC modes. The DC mode is also called the contact mode. The direct contact between probe and sample will cause the mechanical bending of the probe, which can be detected by the listed detection methods in Table 1. The AC mode detects mechanical vibration of the probe, which is usually equal to or close to the mechanical resonant frequency. When the tip closes to the sample surface, the atomic force will change the vibration properties which can be detected by the listed detection method in Table 1. The AC mode can be either a tapping (normal) mode or a shear force mode. In tapping mode, the probe vibrates substantially perpendicular to the sample surface at the contact point. In shear force mode, the probe vibrates substantially parallel to the sample surface.

TABLE 1

Methods of atomic force detection in SPM applications

| | | Atomic Force | | |
|---|---|---|---|---|
| Detection Method | | DC contact | AC tapping | AC shear force |
| Optical detection | Reflection beam | X | X | X |
| | Interference detection | X | X | X |
| | Diffraction beam | N/A | N/A | X |

TABLE 1-continued

Methods of atomic force detection in SPM applications

| | Detection Method | Atomic Force | | |
|---|---|---|---|---|
| | | DC contact | AC tapping | AC shear force |
| Non-optical detection | Electron tunneling current | X | X | X |
| | Tuning fork | N/A | X | X |
| | Other piezo-electric device | X | X | X |
| | Piezo-resistive device | X | X | X |
| | Microwave | X | X | X |

X = combination present

To detect the atomic force induced mechanical changes like bending or vibrating properties, several methods have been developed. These methods can be separated into two categories—optical detection and non-optical detection. The different methods in each category are listed in Table 1 and summarized below.

Exemplary Optical Detection Methods.

Figure 19:
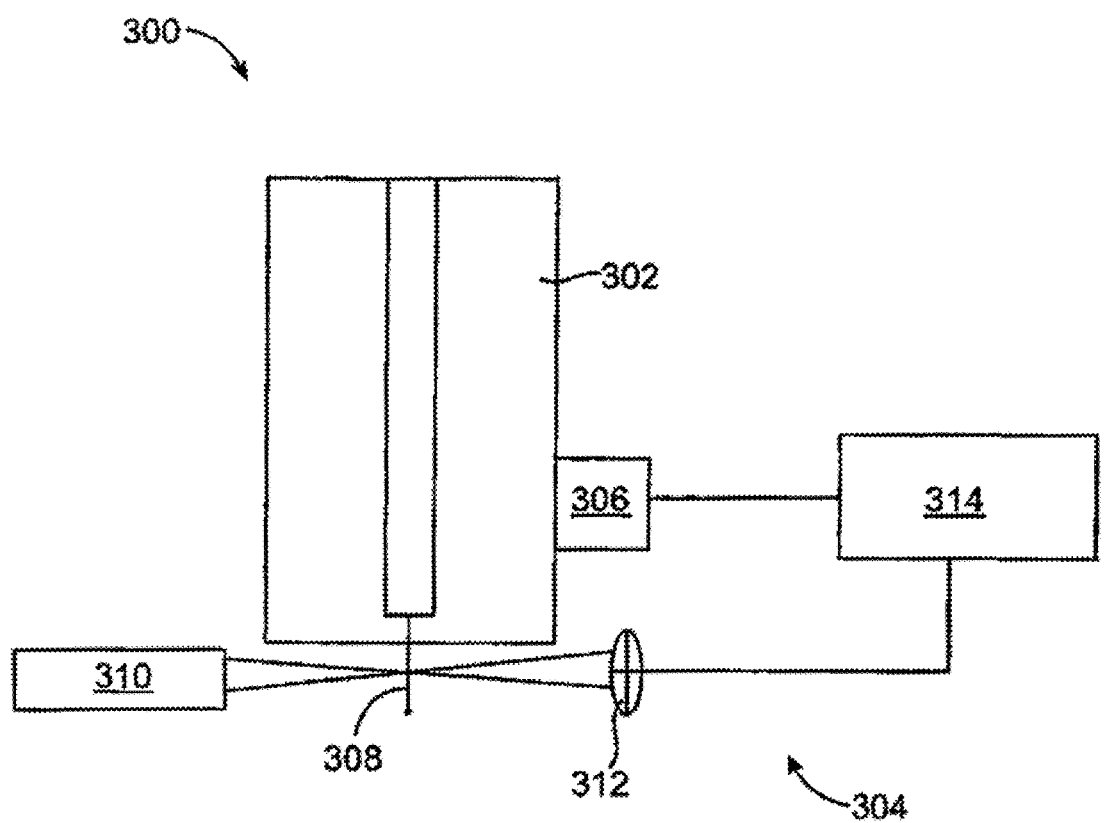
FIG. 19 schematically illustrates an exemplary embodiment of an evanescent wave probe integrated with a scanning probe microscope.

Reflection beam detection: The laser beam is focused on the probe and reflected by the mirror like structure near the end of the probe. The bending or vibration of the probe will cause the change of direction of the reflected laser beam, which can be detected by position sensitive photo diode (PSPD). A PSPD is a square or circle photo diode evenly split in to 2 or 4 independent sections. An example is illustrated in FIG. 19, discussed further below.

Figure 20:
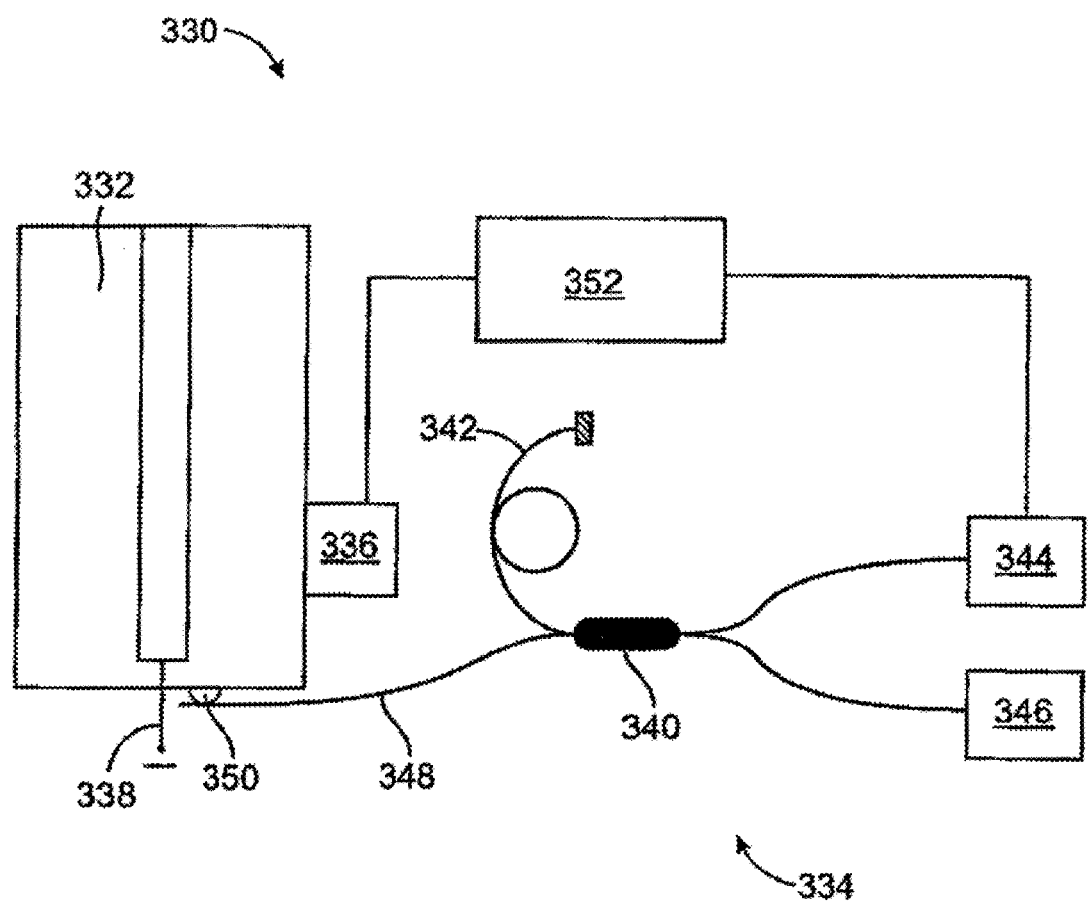
FIG. 20 schematically illustrates another exemplary embodiment of an evanescent wave probe integrated with a scanning probe microscope.

Interferometer detection: A fiber optic interferometer with 1×2 or 2×2 coupler is used to detect the probe bending or vibration amplitude. One flat fiber end of the fiber interferometer is positioned near the front end of the probe. The interference between the reflected light from the probe and the internal reflection of the interferometer can be detected to monitor the probe displacement. For an interferometer with 1×2 coupler, the internal reflection is from the flat fiber end which is facing the probe. For an interferometer with 2×2 coupler, the internal reflection can be the reflection from the other fiber end. Other types of interferometer setups can also been used. An example is illustrated in FIG. 20, discussed further below.

Diffraction beam detection: This method is generally used for shear force mode. The laser beam is focused on the probe and the diffraction spot is detected by a PSPD on the opposite side the probe. When the vibration property of the probe changes due to the shear force, a corresponding change on the diffraction light can be detected by the PSPD.

Exemplary Non-Optical Detection Methods.

Electron tunneling current detection: An electrode is positioned on the metalized back side of AFM probe, the tunneling current between electrode and the AFM probe can be detected so as to know the bending or vibration information of the AFM probe.

Tuning fork detection: The tuning fork is a piezoelectric device which can convert mechanical bending to the electric signal directly. The tuning fork is also a high Q resonant device which is very sensitive to the external force added on either one of its two arms. To detect the atomic force or shear force, one arm of the tuning fork is attached to the probe. The force sensed by the probe can transfer to the tuning fork arms and can be detected by the electronics used to drive the tuning fork.

Other piezoelectric device: Other types of piezoelectric devices can be used to replace the tuning fork as the force sensor. These devices are specially designed to adapt to various types probes and probe constructions.

Piezo-resistive device (e.g., strain gauge detector): The resistance of such device is corresponding to the mechanical strain, which can be used to detect the atomic force instead of the piezoelectric device. An extra piezoelectric device is still need to be used here to generate the mechanical vibrating in AC mode.

Microwave detection: EMP is not only sensitive to the sample impedance, but is also very sensitive to the probe sample distance. The small metal tip protruding from a microwave resonator can be positioned near the SPM probe so that a small capacitance can be built up between them. The bending or vibration of the SPM probe changes the gap between the two probe so that the capacitance between them changes correspondingly. Similar to the principle of EMP, this capacitance change introduces a change in the resonant frequency of the resonator which can be detected by the microwave detection circuits.

All of the exemplary methods and systems disclosed and described herein can be used with EWP systems and devices to form an EWP-SPM combined system. In addition, an EWP-Impedance-SPM combined systems and methods can be formed.

FIG. 19 schematically illustrates an exemplary embodiment of an evanescent wave probe integrated with a scanning probe microscope to result in both spin resonance and scanning probe capability. The exemplary embodiment 300 includes an evanescent wave probe 302 and a scanning probe microscope 304. The evanescent wave probe 302 can be any suitable evanescent wave probe, such as those disclosed and described herein with respect to FIGS. 7A-7B and 11-14B. The scanning probe microscope 304 can be any suitable scanning probe microscope, such as those listed and discussed with respect to Table 1.

In the exemplary embodiment 300, the scanning probe microscope is illustrated as an atomic force microscope with optical detection using a reflected beam. A piezo stack 306 is mounted or coupled to the evanescent wave probe 302. The piezo stack 306 drives the tip 308 of the evanescent wave probe 302 near the tip's mechanical resonant frequency. For shear force mode, the vibration is parallel to the sample surface and perpendicular to the propagation direction of a laser beam emitted from a focused laser source 310. The laser beam and the tip 308 interact in the region of the sample. An atomic force, such as a shear or normal force, is detected by monitoring a change in deflection or position of the tip 308 detected by a sensor 312, such as a quadrant photo diode, as the deflection of the laser from the tip changes. A controller 314, such as a low frequency resonant detection circuit, integrates the control and detection functions of the system.

FIG. 20 schematically illustrates another exemplary embodiment of an evanescent wave probe integrated with a scanning probe microscope to result in both spin resonance and scanning probe capability. The exemplary embodiment 330 includes an evanescent wave probe 332 and a scanning probe microscope 334. The evanescent wave probe 332 can be any suitable evanescent wave probe, such as those disclosed and described herein with respect to FIGS. 7A-7B and 11-14B. The scanning probe microscope 304 can be any suitable scanning probe microscope, such as those listed and discussed with respect to Table 1.

In the exemplary embodiment 330, the scanning probe microscope is illustrated as an atomic force microscope with optical detection using interference detection. A piezo stack 336 is mounted or coupled to the evanescent wave probe 302. The piezo stack 336 drives the tip 338 of the evanescent wave probe 332 near the tip's mechanical resonant frequency. For shear force mode, the vibration is parallel to the sample surface. An atomic force, such as a shear or normal force, is detected with an interferometer 340, such as a fiber interferometer, by monitoring a change in interference pattern between reflected light from the tip 338 and light reflected from the reference arm 342 and detected by a sensor 344, such as a photo diode. The reflected light is supplied by a source 346, such as a laser, and directed to the tip 338 by the sample arm 348. The sample arm can optionally be mounted to the evanescent wave probe by any suitable means, such as by adhesive 350. A controller 352, such as a low frequency resonant detection circuit, integrates the control and detection functions of the system.

By adding the relative detecting features, EMP can also be integrated with other SPMs. An exemplary embodiment is the combination with scanning tunneling microscope (STM). By isolating the microwave resonator probe from the microwave input/output coupler, the bias voltage and current amplifier can be connected to the tip to enable the STM mode. Another exemplary embodiment is the combination with scanning near-field optical microscope. This combination can be realized by changing the metal tip of the EMP into a tapered fiber with a metal coating with a <100 nm fiber aperture at the end. A further exemplary embodiment is the combination with the magnetic force microscope (MFM). This can be realized by attaching a metal coated magnetic particle at the tip end of the EMP.

Further in addition to the above disclosed and described methods and systems including combinations thereof, the methods and systems described in U.S. Provisional Application No. 60/546,056, entitled "Integration of AFM/STM into Evanescent Microwave Probe" filed on Feb. 18, 2004, the entire contents of which are incorporated herein by reference, can be used in the methods, systems and combinations described herein. These methods and systems are further described below.

Atomic force sensor or scanning tunneling microscope probe can be integrated into an evanescent microwave probe (EMP) to form a microscope with the capability of regulating tip-sample distance through atomic force or tunneling current and obtaining simultaneous topology and electrical impedance images.

The describe methods and designs to integrate AFM/STM sensors into evanescent microwave probe. A metal or metalized conductive tip will act both as EMP tip and AFM/STM tip.

In AFM integrated EMP system (EMP-AFM), the EMP tip is either the center conductor of EMP resonator itself or a small metal coated insulating element attached to the center conductor of EMP resonator, with which the microwave signal and atomic force will all be sensed. The atomic force signal can be read out in two ways: electric detection or optical detection. And there are also two operation modes, DC mode, in which the deflection of EMP tip due to the tip-sample atomic force is detected directly, and AC mode, in which the EMP tip is oscillated in or near its resonant frequency and the change of oscillation amplitude, resonant frequency or quality factor will be detected.

In the situation of STM integrated EMP system (EMP-STM), the center conductor tip of EMP is used directly as STM tip. However, to de-couple the interference between microwave signal and tunneling current signal, the EMP resonator coupling loops are designed to be insulated from the resonator cavity.

In one embodiment, a force sensor with electrical read out is attached to the tip of EMP probe and atomic force is sensed by change in sensor mechanical resonant frequency, vibrating amplitude or quality factor. Such sensor can be piezoelectric or piezo-resistive (strain gage sensor). The sensor can be bulk material devices, such as a quartz tuning fork, or thin/thick film device, such as a cantilever coated with piezoelectric or piezo-resistive materials. In this case, the integration of force sensors is possible since the sensors are very small and read out is through electrical signals from piezoelectric or piezo-resistive effect. In the second embodiment, a small force cantilever is mounted near the EMP tip and cantilever tip is electrically connected to the EMP tip. The force is sensed by cantilever through deflection or changes in mechanical resonant frequency, amplitude or Q of the cantilever detected by laser beam deflection. A special configuration is designed in this case to mitigate the conflict between microwave signals of EMP and optical read out signal for cantilever.

In exemplary embodiments, an EMP tip and an AFM/STM tip are combined together so that the microwave signal and AFM/STM signal will be detected simultaneously.

Two example methods to integrate AFM with EMP are disclosed herein, but any suitable integration method can be used. In a first design, the center conductor of EMP resonator is extruded out of EMP cavity and acts as both EMP and atomic force sensing tip. Two techniques can be used to detect the deflection or oscillation of EMP tip. One is to attach a small piezo-electric or piezo-resistive unit to the EMP tip and measure the electric signal resulted from the tip deflection or oscillation. Another technique is to focus a laser beam on a portion of EMP tip and detect the movement of reflected laser beam. For the optical detection scheme, the shape of EMP resonator need to be specially designed to allow the laser beam to pass.

In a second design, an insulating cantilever with tip coated with conductive film is attached to the center conductor of EMP resonator. The metalized tip is electrically connected to the center conductor, which allows the microwave signal to be carried on. The AFM signal can also be read out electrically or by optical means as in the first design.

There are two operation modes for AFM signal detection. In DC mode, the EMP tip contacts with sample during operation. The defection of EMP tip or cantilever due to atomic force is detected. In AC mode, The EMP tip or cantilever is driven by a piezoelectric unit to vibrate in the frequency same as or close to its resonant frequency. The driving piezoelectric unit can be attached to the EMP tip of cantilever directly or to the whole EMP resonator. The change of amplitude, resonant frequency or quality factor of the vibrating tip/cantilever due to atomic force change is detected electrically or optically. In this operation mode, the EMP tip is usually in non-contact with the sample.

Figure 21A:
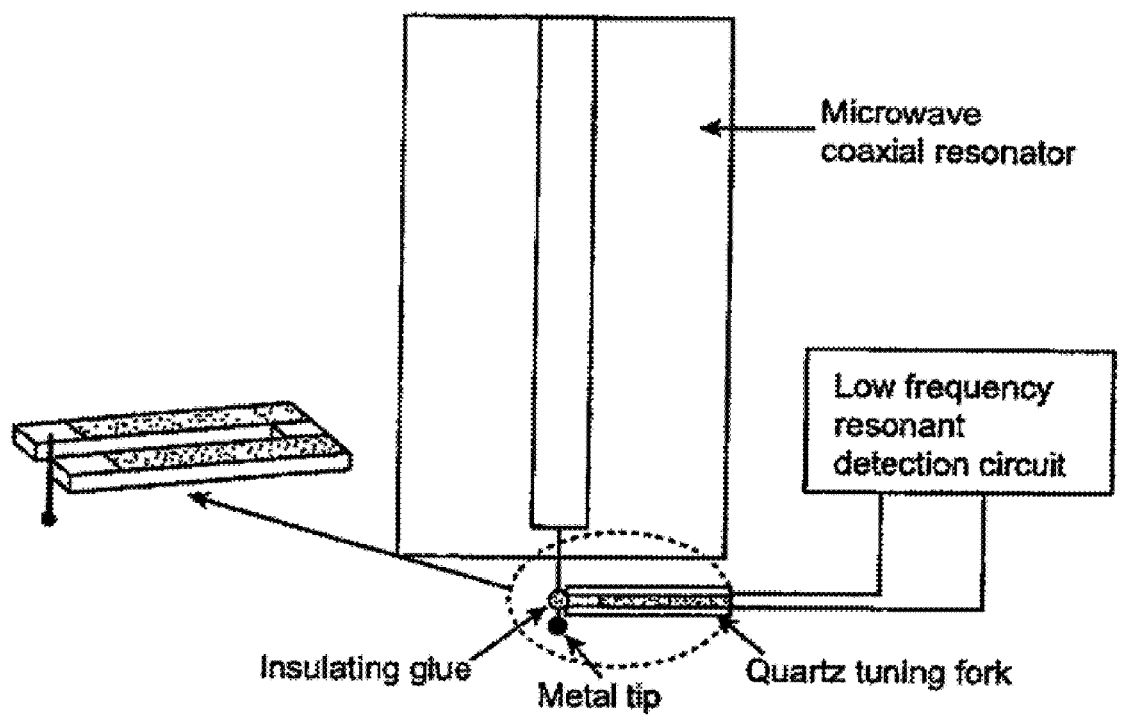
FIGS. 21A and 21B shows an example of EMP-AFM integration, where the quartz tuning fork is mounted with one arm stick with the tip of the microwave resonator as force detector.
Figure 21B:
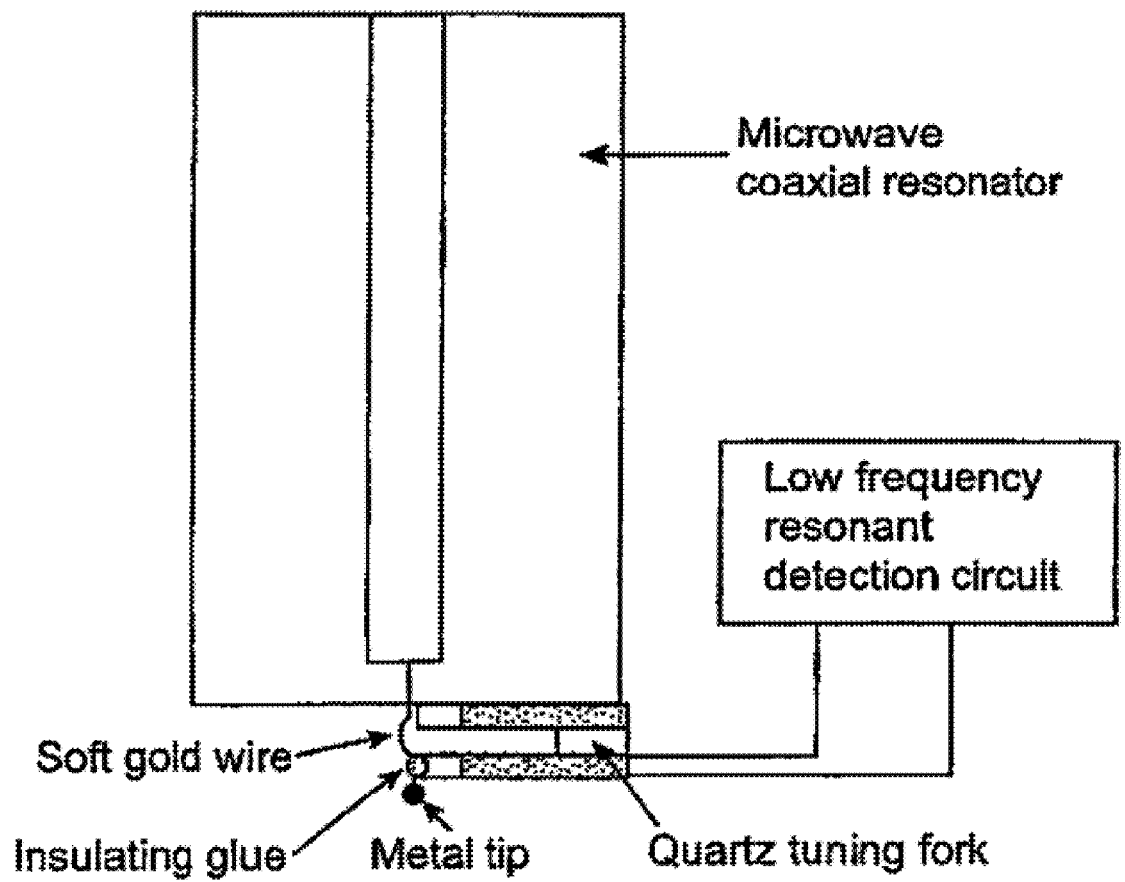

FIGS. 21A and 21B illustrate examples of AFM-EMP integration using a quartz tuning fork as a driving and detection unit at the same time. Preferred configuration of evanescent microwave probe is a dielectrics (or air) filled coaxial resonator with high Q factor in order to achieve high sensitivity. The tip of the EMP is a thin metal wire connected to the center conductor and extruding from a small aperture of end shielding wall (with a preferred outside length of <2 mm). The shielding wall is formed by a metallic thin film (~1-5 microns) deposited on a low loss and low dielectric constant material, such as sapphire. The metal thin film is electrically connected to the outer conductor of the resonator. The tuning fork is fabricated from quartz, such as the one used in commercial clocks/watches or customized. The size of the tuning fork should be as small as possible in order to have high force sensitivity. The adhesive used to attach the EMP tip to one arm of the tuning fork should have low microwave and mechanical loss and be used as little as possible to reduced the effect on tuning fork frequency and Q. The vibration direction of the tuning fork can be either horizontal (shear force as respect to the sample surface, which is shown as FIG. 21A) or vertical (normal atomic force, which is shown as FIG. 21B). The wire from the center conductor of EMP to tuning fork should be thin and soft so that it will not limit the vibration of the tuning fork. The section from the tuning fork to the tip should be short so that the force sensed by the tip can be coupled effectively to the tuning fork. The base of the tuning fork is fixed to the EMP resonator rigidly.

Figure 22:
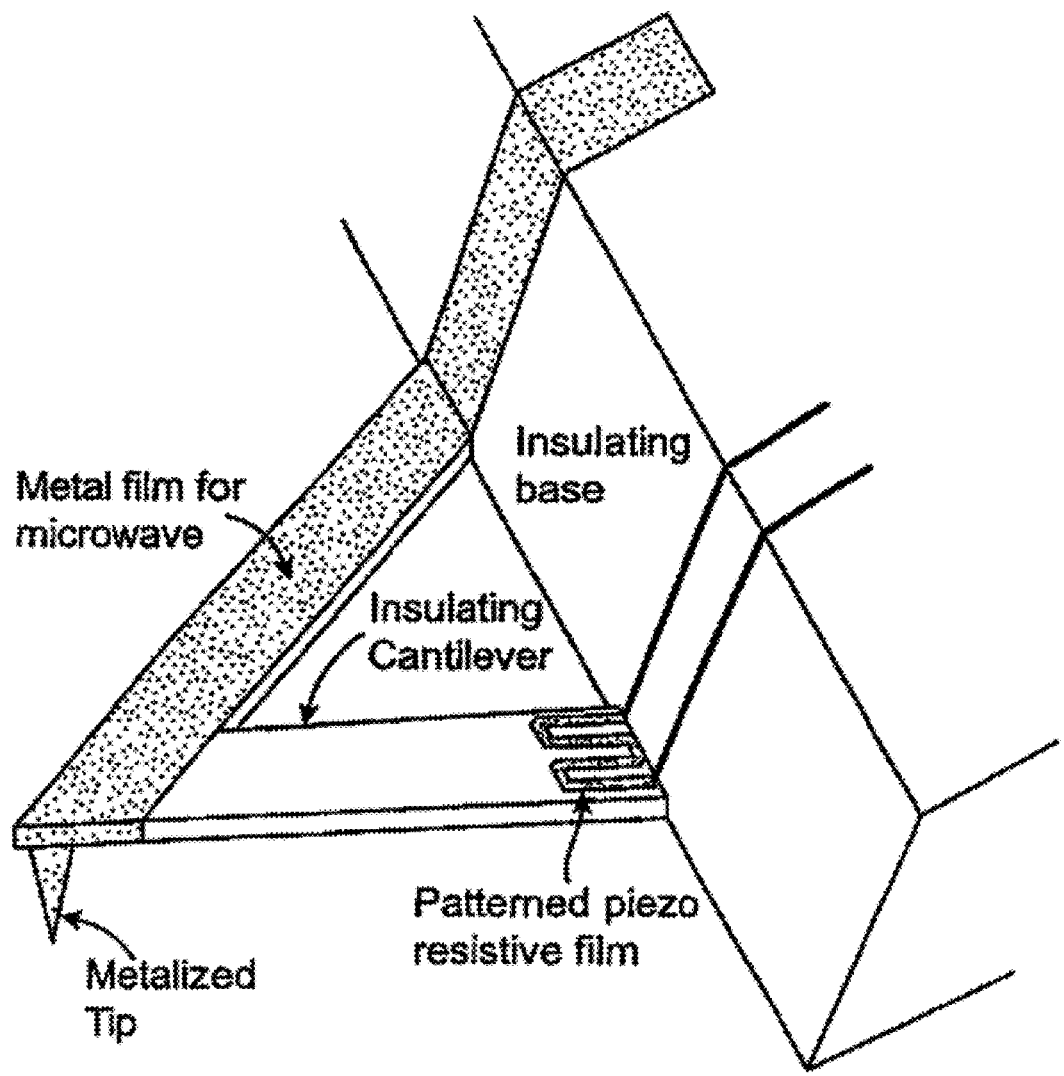
FIG. 22 shows the detail structure of an exemplary cantilever that can be used to transmit microwave signal and detect atomic force simultaneously. A piezo-resistive film is coated to detect the deflection (strain) of the cantilever.

FIG. 22 is another example of AFM signal detection with cantilever and piezo-resistive read-out mechanism. A cantilever is attached to the EMP resonator. The microwave signal from EMP is transmitted to the metalized tip through a metal film coated on one arm of the cantilever. A patterned thin film is coated on another arm of the cantilever with piezoelectric materials to form a strain gage device. When the cantilever is bended by atomic force between tip and the sample, the resistance of the strain gage will change and can be detected by the electronics. The cantilever materials are preferably made of insulating materials such as quartz, glass or silicon nitride since insulating materials will not affect microwave signal of EMP. Other kind of strain gage sensors can also be used here, such as metallic strain gage or silicon strain gage sensors. In order to prevent influence of to the EMP signals, an insulting buffer piece will be used between EMP tip and sensor.

Figure 23:
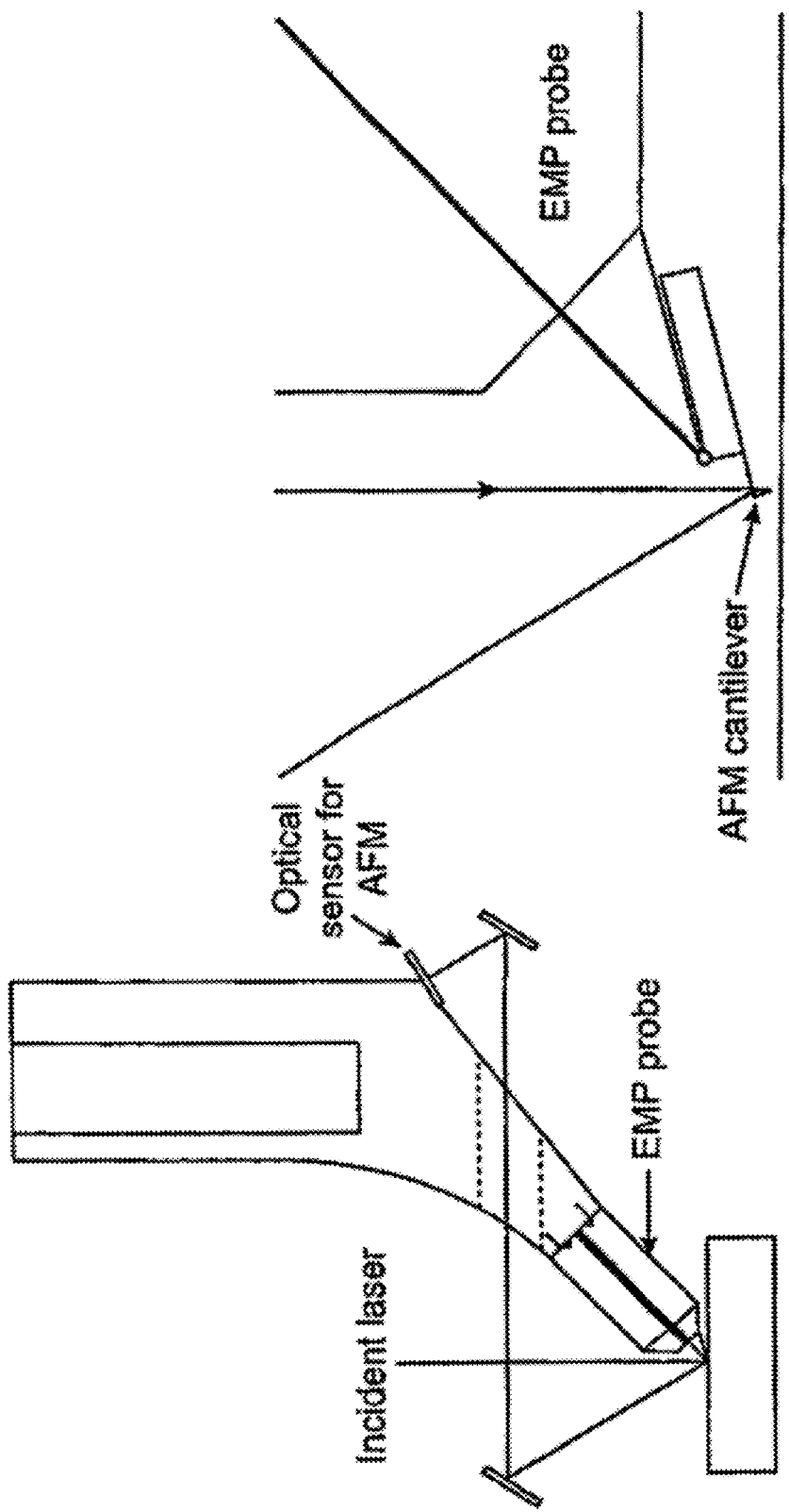
FIG. 23 shows an example of EMP-AFM integration, where an AFM cantilever is attached to the EMP probe as atomic force sensor. The deflection of the cantilever is detected by optical laser beam.

In FIG. 23, an optical detection scheme is used. The EMP is mounted to a fixture, which can then be attached to a scanner. An AFM cantilever is then attached to the EMP probe as shown in the detailed drawing in the right part of FIG. 23. The EMP tip is electrically connected to the tip of AFM cantilever by a thin conducting path. The total connection length from the aperture to the cantilever tip should be as short as possible to achieve high microwave sensitivity, and long enough to allow the laser beam to have access to the tip of the cantilever and reflected to the optic sensor. The total setup can detect the small deflection of AFM cantilever tip in the same way as in ordinary AFM instrument, which has the advantage of easy to integrate EMP to commercial AFM systems.

Figure 24:
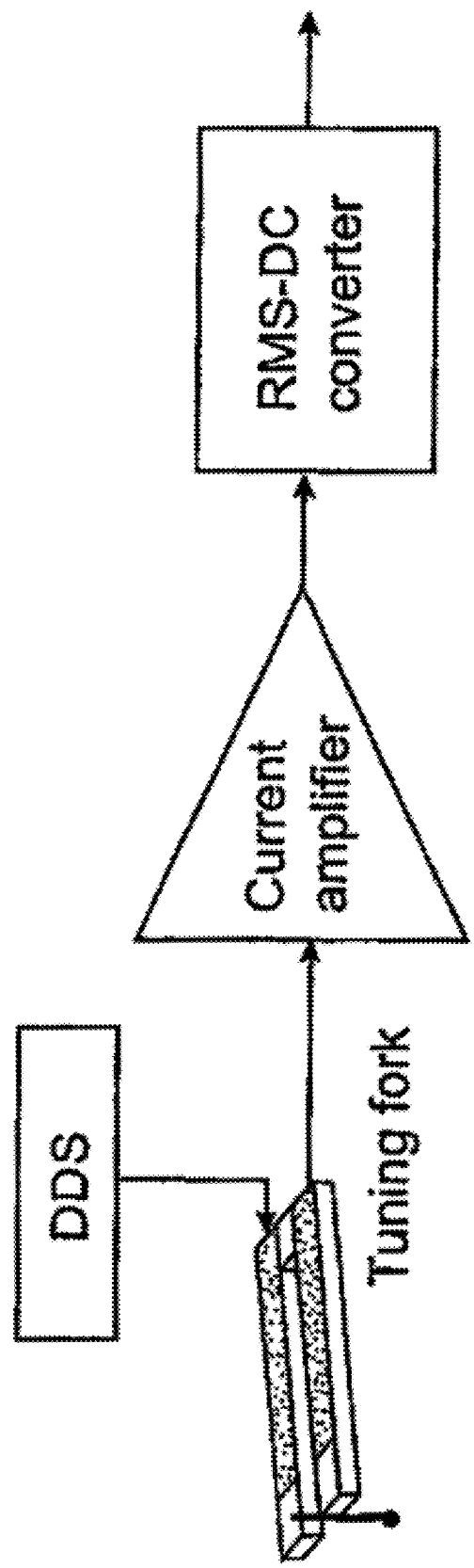
FIG. 24 shows a schematic view of exemplary electronics based on RMS-DC converter, which can be used to translate oscillation signal generated by the tuning fork to DC voltage signal.

For AC mode operation, an electronic circuit is required to drive the force sensor and convert its signal to voltage signal, which can be acquired by the control electronics of the system. The required electronic circuit is determined by the type of force senor. For example, when a tuning fork is used as the force sensor, the atomic force may change the resonant frequency, Q or amplitude of the tuning fork. Several circuit designs can measure such changes, such as RMS-DC converter, Lock-in electronics, or Phase Lock Loop (PLL) device. FIG. 24 shows a design based on the RMS-DC converter. The DDS generate sinusoidal wave to drive the tuning fork at a fixed frequency. The current amplifier will read output. When the tuning fork is driven at resonant frequency, the output signal from the current amplifier has the maximum amplitude. The RMS-DC converter the AC signal to DC voltage with the value equals to the Root Mean Squire (RMS) of the AC signal. When the tip sample is close enough, the atomic force will drag the resonant frequency down, and the driven frequency is no longer equals to the resonant frequency. As a result, the output of the RMS-DC converter will drop down, which can be used as an effective signal to monitor the atomic force.

Figure 25:
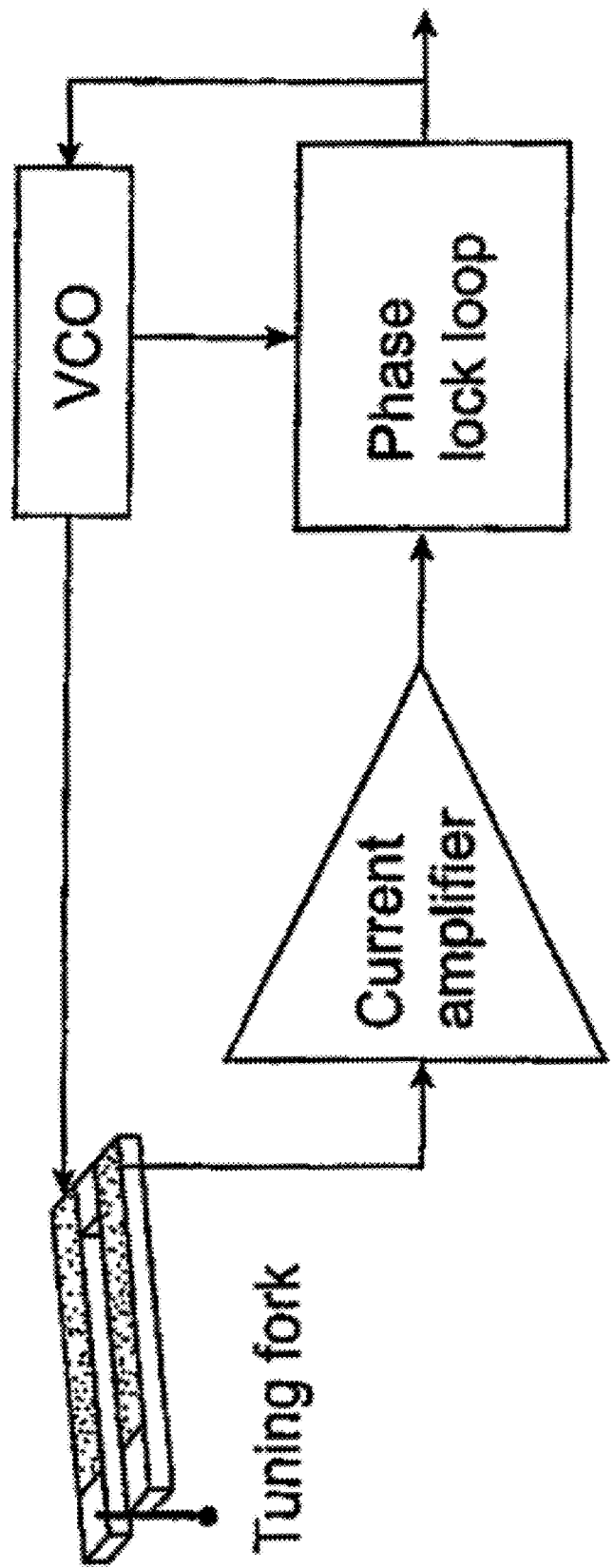
FIG. 25 shows another schematic view of the exemplary electronics based on Phase Lock Loop, which can also be used to track the resonant frequency of tuning fork.

FIG. 25 shows another electronic design to detect the atomic force signal. A Phase Lock Loop (PLL) and a Voltage Controlled Oscillator (VCO) are used to follow the resonant frequency of the resonator. By monitoring the DC control voltage of VCO, the change in resonant frequency caused by the atomic force can be detected.

Figure 26:
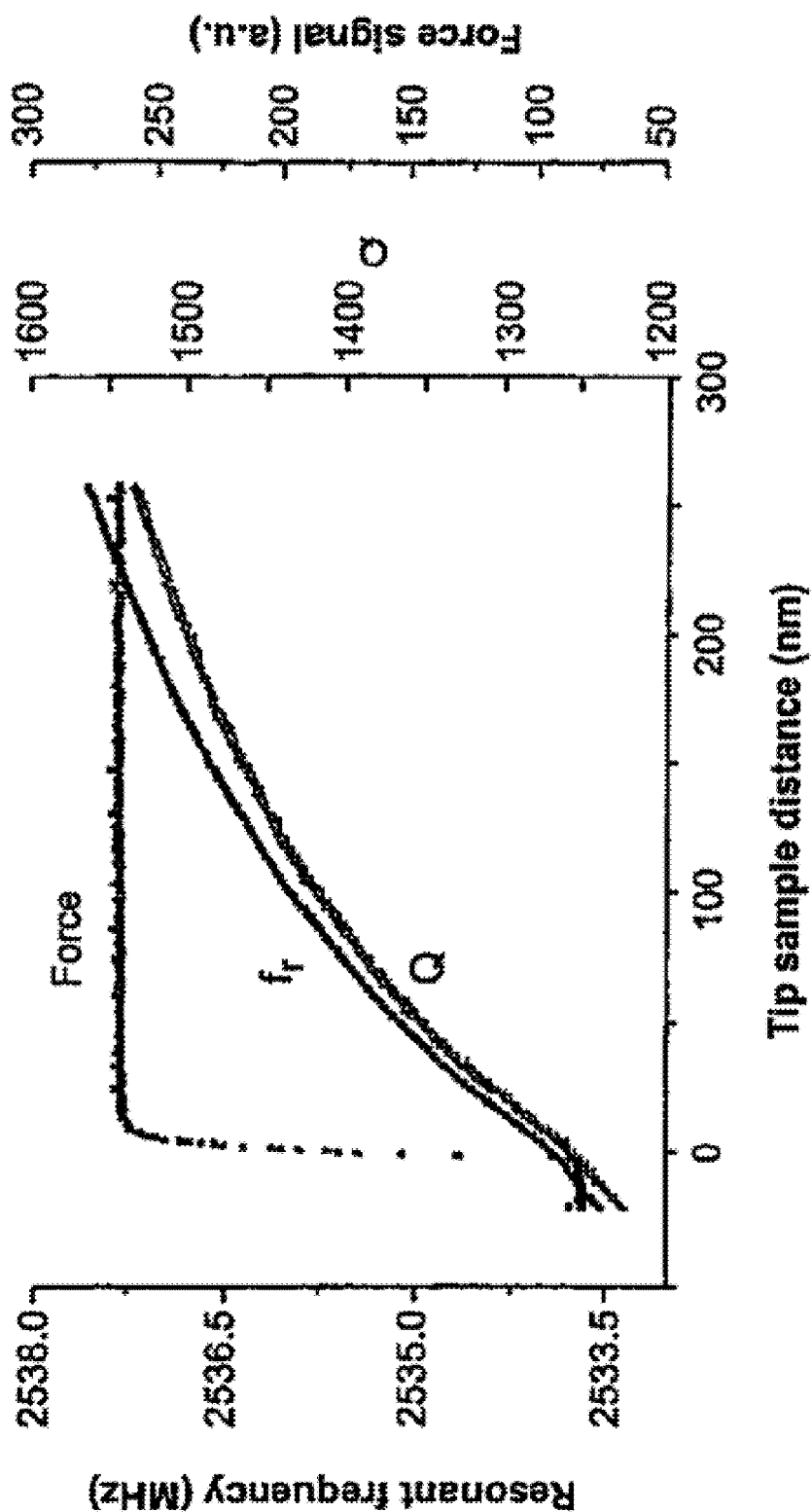
FIG. 26 shows an exemplary approaching curve obtained by the exemplary EMP-AFM system. The resonant frequency, Q of EMP and the force signal are measured simultaneously as function of tip-sample distance.

A real EMP-AFM system based on the tuning fork design has been built and tested. FIG. 26 shows the approaching curve of EMP resonant frequency, Q and atomic force signal as the tip-samples distance is in the range of 300 nm. The tuning fork is used as force sensor to detect shear force as shown in FIG. 21A. The electronic circuit is designed as shown in FIG. 24. As shown, the typical atomic force signal appears when tip sample distance is smaller than about 10 nm, while the microwave signal $f_r$ and Q drops continuously when the tip approaching to the sample. When atomic force signal drop to the bottom, a slightly trend change in $f_r$ and Q signal appears too, which means the tip is in contact with the sample. The sharp drop of the atomic force signal can be used as feedback signal to control the tip-sample distant at a constant value (smaller than 10 nm).

Figure 27:
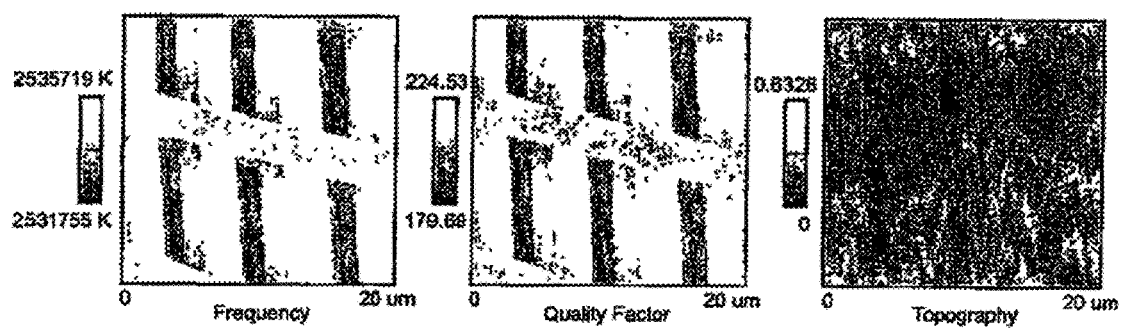
FIG. 27 shows the simultaneous images of microwave and topography obtained by the exemplary EMP-AFM system.

FIG. 27 shows the images of $f_r$, Q and topography scanned by EMP-AFM working in constant force mode. A standard AFM sample is used for the scanning. The sample is patterned with squire holes by low conductive film. The period in X and Y direction are all 10 μm. The step structures shown in each square in the topography image implies the thickness of the film is changing. Since the sheet resistance is determined by the conductivity and the thickness of the film. The $f_r$ and Q images also shown similar structure. An obvious tilting of the sample alignment can be observed in the topography image, but doesn't shown in $f_r$ and Q images, which means the feed back is working very well.

STM with EMP can be integrated. As shown in the exemplary embodiment of FIG. 28, an EMP tip is electrically connected to tunneling current detection circuit and will simultaneously perform STM measurement. The microwave resonator probe is electrically isolated from microwave input/output coupler so that bias voltage and current amplifier can be connected to the tip to enable STM mode. Microwave signal is coupled into or out from the resonator through an isolated coupling kit. During measurement, the tunneling current can be used as a feedback signal to regulate the tip-sample distance. Integration with STM and an evanescent wave probe for studying library members will be examined more fully in the next section.

Evanescent Wave Probe Techniques in Conjunction with Scanning Tunneling Microscopy As discussed above, embodiments of the present evanescent wave probe may be used to examine library members using high-resolution, high-sensitivity nuclear spin resonance and/or electron spin resonance detection techniques in conjunction with scanning tunneling microscopy. In the following section, evanescent wave probe techniques will be discussed along with a discussion of scanning tunneling microscopy (STM), and techniques by which the two may be integrated. Included in the discussion will be pulsed electron resonance spin (ESR) techniques that may be used with the integrated EWP-STM probe, as well as optical pumping techniques that may be used to excite the precessing spin state.

Embodiments of the presently integrated EWP-STM design emphasize the ability of the EWP probe to excite, pick up and enhance spin resonance signal from sample. Advantages of the current design include an unprecedented flexibility in setting experimental parameters such that the desired resonance signal may be detected. For example, to distinguish the modulated tunneling current from the EWP sensed signal (where "EWP sensed signal" means the signal detected directly by the EWP probe, rather than through the tunneling current), the tip-sample distance or tunneling bias voltage may be changed and/or modulated, and thus the ESR signal may be detected according to the tip-sample distance or bias voltage change. That portion of the ESR signal which is related to the bias voltage change is ideally contributed by the tunneling current component, and the other portion is the EWP inductively sensed signal directly from the sample rather than through the tunneling current. This technique provides a unique capability for conducting electron spin resonance spectroscopy from a single atom or molecule of a sample.

Integrated EWP and STM Tip Structures

The evanescent microwave probe is a highly sensitive spin resonance detection technique that operates by sending microwaves generated from a microwave resonator to a conducting tip that is part of the evanescent microwave probe, which then sends evanescent microwaves into a sample. The results of that interaction are then detected by the same EWP tip. Evanescent waves are generated by the EWP tip because the tip radius is much less than the wavelength of the microwaves in question. This interaction between the sample and the evanescent microwaves delivered from the EWP tip depend on the complex electrical-magnetic impedance of the sample. The interaction depends on both the real and the imaginary parts of the impedance, and thus there are changes in resonant frequency ($f_r$) and quality factor (Q) of the resonator. Advantages of the present embodiments are that the EWP can simultaneously measure both the real and imaginary parts of the sample's electrical impedance, as well as the surface topography, by detecting the shift in resonance frequency and quality factor of the resonator as a result of the interaction. It will be understood by those skilled in the art that evanescent waves, also known as near-field waves, differ from far-field waves in that evanescent waves do not radiate or propagate in space, and are localized to (and only present near) the surface of the sharp, conducting, EWP tip. Evanescent (near-field) waves have a much higher spatial resolution than propagating (far-field) waves, and the enhanced resolution is on the order of the wavelength ($\lambda$) of the wave. The evanescent waves of the present embodiments may have energy in either the RF or microwave region of the spectrum.

To achieve even better spatial resolution, down to the atomic level, and enhanced sensitivity that can detect a single spin resonance, the present embodiments implement an approach based on the detection of electron and/or nuclear spin resonance via a tunneling current used in conjunction with the inventors' EWP technology. In this approach, tip of the evanescent wave probe (EWP) also serves as the tip for a scanning tunneling microscope (STM), and thus it is possible to simultaneously perform electron-tunneling measurements with the measurements previously disclosed for the EWP.

Figure 28:
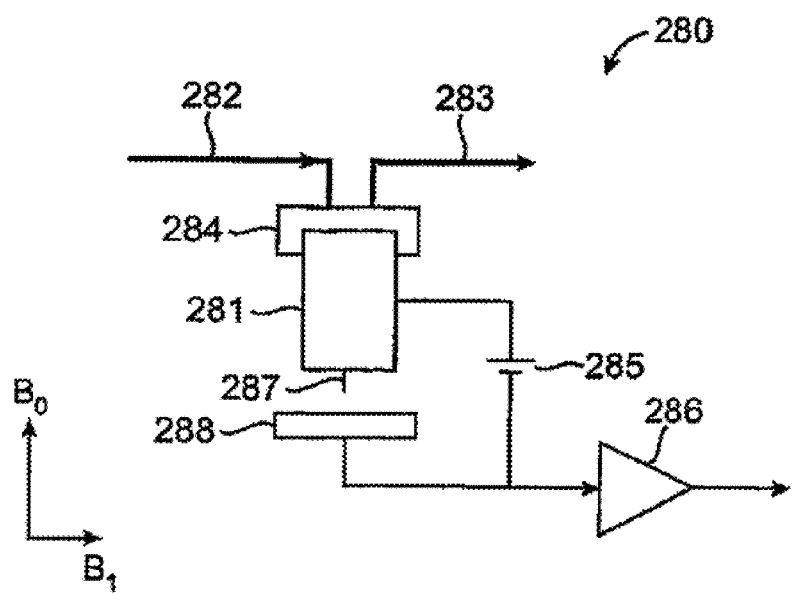
FIG. 28 is a schematic illustration of an integrated EWP-STM instrument design at the level of the resonator, sample, and tunneling current circuit.

An integrated EWP-STM system is shown generally at 2800 in FIG. 28. Referring to FIG. 28, a microwave resonator probe comprises a resonator cavity 281, which is electrically isolated from the microwave (or RF) input 282 and output 283 through a coupling kit 284, such that a bias voltage 285 and current amplifier 286 can be connected to the EWP/STM tip 287 to enable the STM mode. The microwave signal is coupled into or out of the resonator 281 via the isolated coupling kit 284. The sample is located at reference numeral 288 in FIG. 28, and it immersed in a static magnetic field $B_0$, where it is usually desired to have this externally applied magnetic field $B_0$ be as uniform as possible. Thus, the EWP probe may be operated as an electron spin resonance excitation source (which may be operated in a radio frequency range), and/or passively as a microwave detector. Since the STM and EWP probe share the same tip, and thus the modulation signal of the tunneling current, which was induced by the spin resonance, will be coupled into EWP-STM probe.

The present design illustrated in FIG. 28 dramatically increases the detection sensitivity since the resonator provides a substantially ideal impedance match between the tunneling and microwave circuits. An additional advantage is that the signal derived from the microwave modulation of the tunneling current will be resonantly enhanced by about a factor of Q (i.e., from about 10 to 1,000) before being amplified by the low noise microwave amplifier.

Separated STM and EWP Tip Structures

Figure 29:
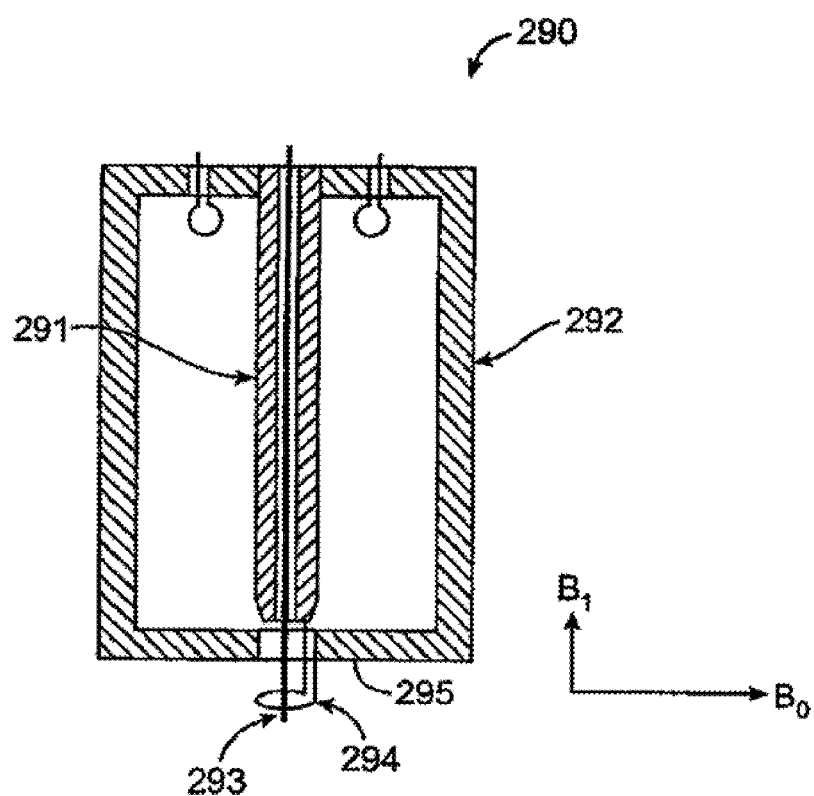
FIG. 29 shows an exemplary EWP-STM probe tip, in this case where the STM tip and an EWP loop are separate structures.

An alternative embodiment is illustrated in FIG. 29, where the probe tip of an exemplary integrated EWP-STM system has separate STM tip and EWP loop structures. Referring to FIG. 29, the microwave or RF generator shown generally at 290 comprises an EWP center conductor 291 within EWP resonator cavity 292, STM tip 293, and EWP loop 294. In this case, the EWP tip of previous embodiments is replaced by loop structure 294. The conductive loop 294 is electrically connected to the EWP cavity center conductor 291, and the outside shielding wall 295, and lies in the horizontal plane perpendicular to the center axis of the cavity 292. The STM tip 293 extends throughout the length of the EWP cavity 292, and is inside and coaxial with the center conductor 291, but is in electrical isolation to the EWP probe 290. Additionally, the STM tip 23 extends through the center of the loop 294.

Advantages of the EWP-STM structure depicted in FIG. 29 are that the small EWP loop 294 is contemplated to produce a magnetic field several orders of magnitude higher than the magnetic fields produced by other configurations. This can be especially advantageous for sensitivity enhancement or in critical applications requiring a condition of strong magnetic field. In the following discussion an intrinsic spin resonance sensitivity analysis is provided based on EWP direct spin resonance detection with a loop structure using a pulse technique; however, the same principles apply to the present EWP-STM structures with regard to the relationships between sensitivity, loop dimensions, and noise analysis.

As discussed by D. I. Hoult and N. S. Ginsberg in an article titled, "The quantum origins of the free induction decay signal and spin noise," Journal of Magnetic Resonance, 148, pp. 182-199 (2001) the electrical field generated by a small sample with a time varying magnetic moment $\vec{M}$ is given by (in SI units):

$$\vec{E} = \left(\frac{\mu_0}{4\pi r^3}\right)\vec{r} \times \left(\vec{m} + \frac{r}{c}\ddot{\vec{M}}\right) \quad (1)$$

Assuming the receiving coil has radius $r_0$ with coil plane normal direction in the x-y plane, the external magnetic field $\vec{B}_0$ is along z axis, and the sample located in the coil center has negligible spatial extent (most applicable for intrinsic sensitivity analysis since only a very small number of spins are involved here) with spin moment $\vec{M}$ rotating inside x-y plane at Larmor frequency $\omega_0$, the electric field generated along receiving coil is:

$$E = \frac{\mu_0 \omega_0 M_0}{4\pi r_0^2}\left(1 + i\frac{r_0 \omega_0}{c}\right)e^{i\omega_0 t} \quad (2)$$

The first term of equation (2) is the effect of near field Faraday induction, and second term is the radiation term (which can propagate to the far field). It will be apparent to one skilled in the art that, in a low frequency range and with a small pick up coil radius (a condition applicable to substantially all NMR spectroscopy instruments), a near field induction effect dominates, while in a high frequency range and with large receiving loop radius situations, the radiation term (applicable to most MRI and ESR high frequency instruments), is proportional to $r_0\omega_0/c=2\pi r_0/\lambda$, and this term may dominate the effect. Careful evaluation of these two different mechanisms and attention paid to the consequences of a frequency and radius dependence, have not to the inventors' knowledge been practiced in any previous sensitivity analysis.

In the case of the present evanescent wave spin resonance probe, an evanescent wave condition ($2\pi r_0/\lambda \leq 1$) is always satisfied, so that radiation term is always smaller than near field induction term. The maximum signal power (the induction term) the receiving coil with n turns could generate as a signal output is given by:

$$P_S = \frac{n^2}{32} \frac{\mu_0^2 \omega_0^2 M_0^2}{r_0^2} \frac{1}{R_C} \quad (3)$$

where $R_C$ is the coil's RF resistance, and $$R_C = n \frac{2\pi r_0}{d} \sqrt{\frac{\mu_0 \omega_0}{2\sigma}}$$

with coil cross dimension d and conductivity $\sigma$. The magnetic moment $M_0$ of sample volume $V_S$ is given by:

$$M_0 = V_s \chi_0 B_0 / \mu_0 \quad (4)$$

$$= Ng\mu_B J(J+1)\frac{\hbar\omega_0}{3kT}$$

where $\mu_B$ is the Bohr magneton for electron spin.

The intrinsic minimum detectable spin number is limited by coil output Johnson noise:

$$N_{min} = \frac{24\sqrt{\pi}}{\hbar\mu_0^{3/4} g\mu_B J(J+1)(2\sigma)^{1/4}\sqrt{Nd}} r_0^{3/2} \omega_0^{-7/4} (kT)^{3/2} (\Delta B)^{1/2} \quad (5)$$

This parameter is proportional to $r_0^{3/2}\omega_0^{-7/4}(\Delta B)^{1/2}$. To increase the sensitivity, embodiments of the present invention advantageously select a high excitation frequency, low detection bandwidth, and most importantly, a small loop radius. This relation clearly points out the important consequence of having a small curvature evanescent probe as the detection probe for spin resonance.

Furthermore, the above formula teaches the effect of a spin population difference at a given temperature. Since in some embodiments of the present invention it is possible to overcome this problem; i.e. by having fully polarized spins even at room temperature, the above formula may be written without including this factor:

$$N_{min} \approx \frac{8\sqrt{\pi}}{\mu_0^{3/4} g\mu_B J(J+1)(2\sigma)^{1/4}\sqrt{Nd}} r_0^{3/2} \omega_0^{-3/4} (kT\Delta B)^{1/2} \quad (6)$$

An exemplary embodiment provides for a single turn copper loop with a radius of 10 μm and a cross dimension of 2 μm, such that with a 9.4 GHz excitation frequency and a 4.2 K temperature, an intrinsic ESR sensitivity of $3.7\times10^2$ spin/$\sqrt{Hz}$ may be realized.

In the EWP-STM structure depicted in FIG. 29, the microwave frequency modulation of the STM tunneling current (which is DC) is coupled to the EWP loop 294, and therefore spin resonance information may be conveyed to the EWP probe 294 via the tunneling modulation signal.

Pulsed ESR Techniques

One of the most important advances in NMR spectroscopy occurred roughly two decades ago with the development of pulsed (time resolved) Fourier transformation (FT) instrumentation. There are several key advantages offered by the pulsed Fourier transform technique. First, the sensitivity of an instrument can be potentially vastly improved relative to continuous wave (CW) techniques. Second, the pulsed Fourier transform technique is capable of performing spin echo and other higher dimensional quantum correlation experiments.

The ability to perform spin echo experiments with a scanning tunneling microscope setup is significant. Previously reported ESR-STM experiments relied upon random thermal fluctuations (or even unknown, or unclear mechanisms) to generate the mixed Zeeman states necessary for the observation of a modulated tunneling current. Only a very few materials systems have been reported to show such phenomena, and then only under very special conditions. According to embodiments of the present invention, pulsed ESR techniques in conventional spin echo or two-dimensional Fourier transform electron spin resonance (2D-FT-ESR) spectroscopy may be utilized to excite coherently precessing mixed spin states of electrons to ensure the modulation of a tunneling current by the spin resonance in a sample.

Figure 30:
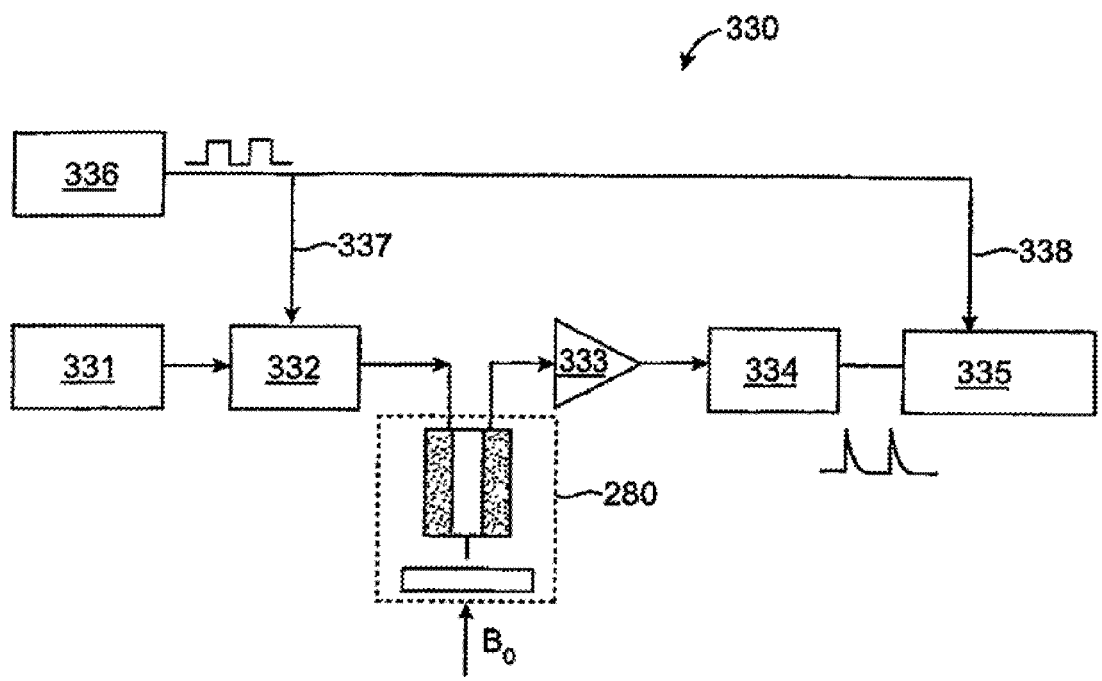
FIG. 30 is a schematic illustration of the present EWP-STM integrated probe with electronics (shown in block format) that may be used to operate the probe in a pulsed configuration for detecting spin resonance.

An exemplary system for carrying out such a pulsed excitation experiment to detect electron spin resonance using the present EWP-STM technique is illustrated in FIG. 30. Referring to FIG. 30, an EWP-STM system configured to conduct pulsed experiments is shown generally at 30. It comprises an integrated EWP-STM probe 280, which has already been discussed in reference to FIG. 28 or FIG. 29, receiving input energy from an RF source 331 via a switch 332. The output signal from probe 280 is first passed to a low noise amplifier 333, whereupon the amplified signal is sent to detector 334 and data acquisition system 335. Pulsing of the RF input signal is provided by pulse generator 336, which provides a trigger signal 337 to the switch 332, as well as a trigger signal 338 to the data acquisition system 335.

In one method of using the apparatus of the present embodiments, an initial π/2 radio frequency (RF) pulse emitted by the EWP component of the probe creates an initial local electron spin state on the sample surface, where the spins are transverse to the external magnetic field $B_0$. Each electron's spin wave function in such an initial state is actually a coherent superposition of spin-up and spin-down eigenstates, which are split in the magnetic field by the Zeeman energy $\Delta E = g\mu_B B$. Coherent evolution under the spin Hamiltonian results in an oscillation between the two eigenstates. Classically, this oscillation corresponds to the precession of the spin vector at the Larmor frequency $\Delta E/\hbar$ in a plane normal to the applied magnetic field. This kind of spin oscillation (or precession) will therefore introduce a modulation of the tunneling current in a frequency equal to Larmor frequency.

In an alternative embodiment, a series of RF pulses may be delivered to the sample after the initial excitation pulse.

EWP-STM and the Spin Echo Technique

In the present embodiments, the spin echo technique is used to overcome the quantum de-coherence of spins that can occur as a result of the randomization of spin directions; a phenomenon known as spin-spin relaxation, and characterized by the transverse relaxation time $T_2$. A "spin echo" is created when a transverse magnetization is created in the sample by applying a 90° radiofrequency pulse; the transverse magnetization then decays away as a result of a spreading out of frequencies due to inhomogeneities in the applied $B_0$ field; the 90° pulse is then followed by a 180° pulse, which refocuses the transverse magnetization such that it grows back to form an echo. The spin echo technique is useful because it can mitigate the effects of both inhomogeneities in the applied $B_0$ field, and chemical shifts arising from the chemistry of the sample.

Most commercially available ESR spectrometers are still of the conventional continuous wave (CW) design, and only limited academic efforts have been made to adapt pulse techniques to ESR. There are at least two reasons for this. First, most ESR experiments involve relaxation times that are much shorter than those encountered in NMR, and second, it is difficult to reduce the ESR system relaxation time (known in the art as "dead time") to below the sample relaxation time, a necessary condition if meaningful information is to be extracted. Spin echo experiments apply an intense microwave radiation pulse to the sample to rotate electron spins by angles of either $\pi/2$ (to create the transverse magnetization), or $\pi$ (to refocus the transverse magnetization) in a time period that is much shorter than either the spin-lattice relaxation time $T_1$ or the spin-spin relaxation time $T_2$. Input microwave powers on the order of several thousand watts are typically required, which is orders of magnitude larger than the ESR signal. The ESR signal is so small that it can generally be detected only after the intense excitation power has decayed to a level that is within the dynamic range of the detection electronics; this decay time is defined as "dead time." The dead time has to be short enough so that the ESR signal decay due to the spin-lattice and spin-spin relaxation mechanisms (quantified by $T_1$ and $T_2$, respectively) is not so strong as to have completely quenched the ESR signal prior to the expiration of the dead time. State of art experimental set-ups (in existence at just a few universities) have demonstrated dead times on the order of 50 to 150 nanoseconds; as a consequence, only a very limited number of sample systems may be investigated.

The dead time $T_d$ can be calculated using the following equation:

$$T_d = (P_s - P_r)/d_r \quad (7)$$

where $P_s$ is the input excitation signal power in units of dBm, $P_r$ is highest detectable power level (dBm) within detection system's dynamic range, and $d_r$ is the resonator power damping rate (dB/s) given by:

$$d_r = -10\log\left(\exp\left(-\frac{1}{\tau_r}\right)\right) = \frac{4.34}{\tau_r} \quad (8)$$

In equation (8), the resonator time constant $\tau_r = Q_L/f_0$ with quality factor $Q_L$ and resonant frequency $f_0$. From the dead time equation, one skilled in the art will note that the dead time is shorter with lower input signal power or lower $Q_L$.

Embodiments of the present EWP-STM design address these deficiencies that have existed in the art to date. Due to the small curvature tip of EWP probe, a $B_1$ field can be provided that is as high as any of those contemplated to be required, and these exceptionally high fields may be generated with an input power 282 to the resonator 281 as low as about 10 to 100 milliwatts. In other words, the input resonator power that is required to generate any field necessary is at 4 orders of magnitude less than that the power required in conventional ESR systems. As a consequence, due to the exponential nature of the decay, this present EWP-STM systems realize dead times that are at least 4 times shorter than the dead times demonstrated by state of art ESR set-ups, given the same $B_1$ field, operating frequency, and electronics dynamic range. Furthermore, it is contemplated that with the small excitation signal levels, faster microwave switches and other components may be used to reach an intrinsic limit of the dead time. Even further improvements (reductions in dead time) may be realized by implementing an EWP-STM design comprising a bimodal resonator structure with orthogonal modes.

It is contemplated that a dead time as low as about 5 to 10 nanoseconds may be achieved with the improvements offered by the present EWP-STM embodiments. With such an instrument available, it will become feasible to perform pulse spin echo experiments on a much wider range of sample types than is currently available.

EWP-STM and Optical Pumping

Figure 31:
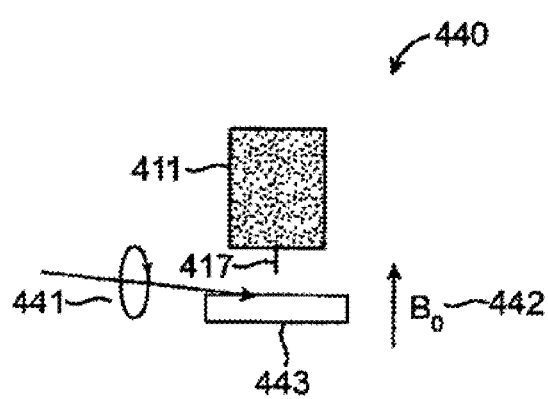
FIG. 31 is a schematic illustration of an optical pumping scheme for detecting electron spin resonance.

Optical pumping is another technique that can be used to excite precessing spin states. As illustrated in FIG. 31, the optically pumped EWP-STM system shown generally at reference numeral 440 comprises a circularly polarized laser pulse 441 aligned perpendicularly to an applied external magnetic field 442. The polarized laser pulse 441 is directed toward a surface of a sample 443. In one embodiment of the present invention, the sample 443 may be a semiconductor.

For the purposes of the present description, it will be assumed that the sample 443 is a semiconductor. According to the present embodiments, the circularly polarized laser pulse 441 creates an initial electronic state in the conduction band of the semiconductor sample 443 in which all the optically excited spins are oriented in a transverse direction relative to the external magnetic field 442. Repetitive laser pulses may be applied to the semiconductor sample 443 to resonantly build spin precession; if this is the case, then it is desirable to set the interval of pulses to a value such that the precession frequency maintains the electron spins in phase for successive pulses. Incoherent evolution of the spin's wave function will usually result in a departure from a smooth oscillatory behavior. Therefore, by increasing the interval of successive pulses, and measuring the change in the amplitude of the tunneling current, a spin decay behavior can be measured and correlated to spin relaxation time.

These embodiments are contemplated to be capable of enabling spin resonance detection in a wide range of materials systems. For example, semiconductor materials will most likely be used in quantum computing application, and due to the small population difference between Zeeman states of the participating electrons, optical pumping techniques will be high advantageous in conjunction with the present EWP-STM embodiments to generate an initial precessing spin state for the system.

The Evanescent Wave Probe with Enhanced Resolution and Sensitivity

The present inventors have developed a novel scanning evanescent microwave probe (SEMP) having a shielding structure that is designed to confine propagating far-field components to the resonant cavity. Thus, only non-propagating evanescent waves are generated at the tip of the probe. The inventors had also developed theoretical models to obtain near-field analytical solutions to the relevant mathematical equations, the models allowing for quantitative measurements to be made of the electrical impedance of materials in the microwave domain with sub-micron resolution. These developments represented significant progress in the field of non-destructive and quantitative electrical impedance measurements, and they could be applied to a wide range of materials ranging from insulating dielectrics, to semiconductors, to highly conducting metals. The EMP disclosed previously emits evanescent microwaves into the sample via a conducting tip that is part of the probe; the same tip of the probe then detects the result of the interaction of the evanescent waves with the sample. The interaction of the evanescent waves with the sample causes changes in the resonant frequency and quality factor of the microwave resonator. The electrical impedance being measured is complex in mathematical terms; that is to say, the impedance includes both real and imaginary components.

Probe Shielding

The novel scanning evanescent microwave probe (SEMP) developed by the inventors has, ideally, a shielding aperture that is small, and a tip section that extends outside the aperture that is short, to achieve the best shielding effects. However, in practice these effects are difficult to achieve since a large flat probe surface is difficult to scan over the flat surface of a sample without damaging the sample. In previous embodiments of the present inventors' microscope, the tip section that extended outside the shielding aperture had been restricted to a few mm in length to achieve the scanning function. A further advantage of lengthening the tip was an enhanced ability to implement and monitor a desired tip-sample distance through atomic force sensing. Extending this tip section, however, may create a measurable far field effect, which can be detrimental to quantitative metrology applications. In particular, extending the tip section may reduce the true spatial resolution of the instrument.

Figure 32A:
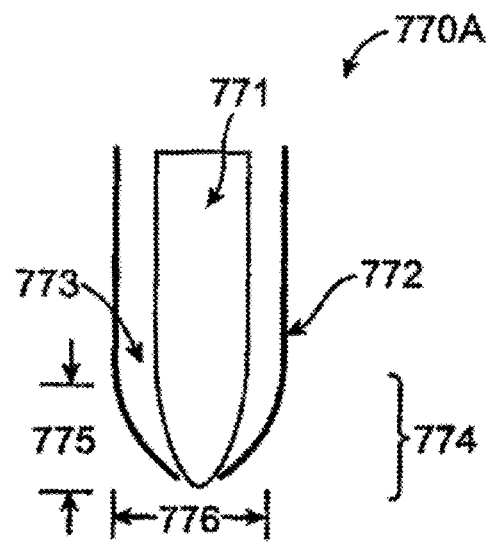
FIGS. 32A-B show detailed structures of coaxial probe tips that are shielded; with a small and wide angle of tapering, respectively.

Detailed structures of a coaxial shielded tip having a tapered region are shown in FIGS. 32A, B. The probe tip shown generally at 770A in FIG. 32A comprises a center conductor 771, a shielding 772, and an insulating material 773A positioned outside of the conductor 771, but inside of the shielding 772. The tapered region shown generally at 774 in FIG. 32A is "bullet-shaped," and is configured such that the length 775 of the tapered region 774 is about on the order of the dimension of the diameter of the tip (center conductor 771 plus insulating material 773A), wherein the diameter is represented by reference numeral 776 in FIG. 32A.

Figure 32B:
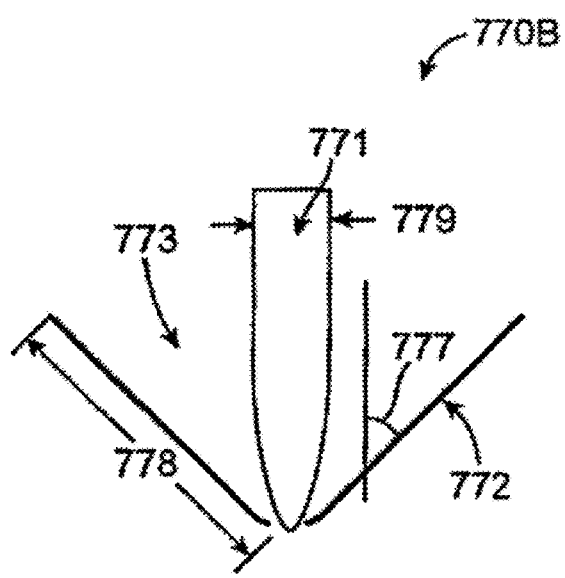

A different configuration of a tapered tip is shown in FIG. 32B, where the probe tip shown generally at 770B has substantially the same center conductor 771, surrounded by an insulating material 773B (which may be the same type of insulating material as insulating material 773A, but of course will be in a different shape). The taper of probe 770B may best be described by the angle 777 that the shielding 772B makes with a center line of the center conductor 771. In embodiments of the present invention, angle 777 ranges from about 10 to 90 degrees. The configuration of the tapered region of probe 770B may also be characterized by the length 778 of the taper; in embodiments of the present invention, length 778 may range as anywhere from one half of the diameter 779 of the central conductor 771, to 100 times the diameter 771.

Figure 33A:
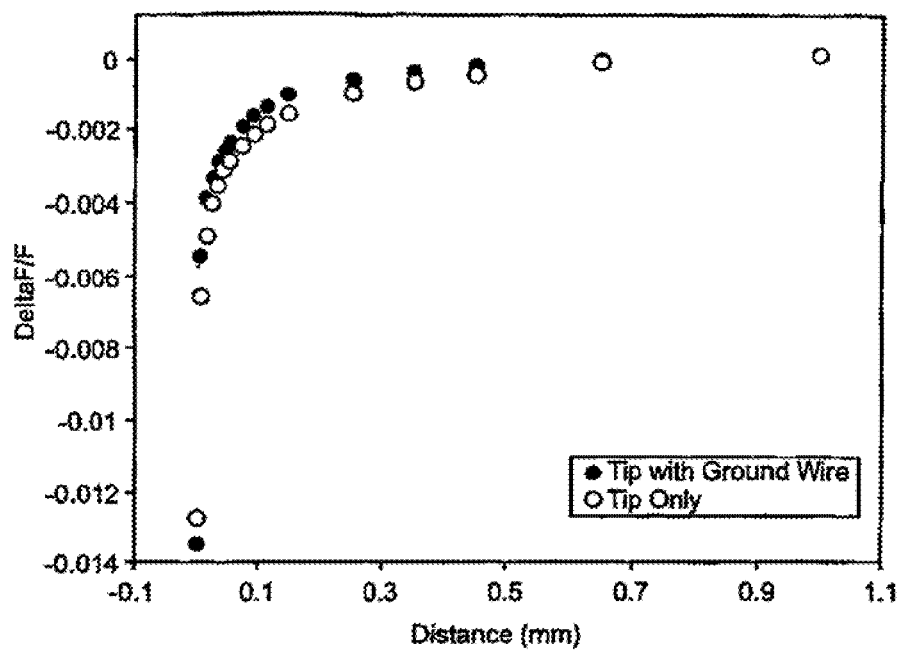
FIGS. 33A-B are graphs illustrating the resonant frequency change of an exemplary EWP as the probe tip approaches a metal sample surface; the tips in FIG. 8 compare an open tip and a ground wire balanced tip; the two curves in FIG. 8 compare an open tip to a tip with shielding.
Figure 33B:
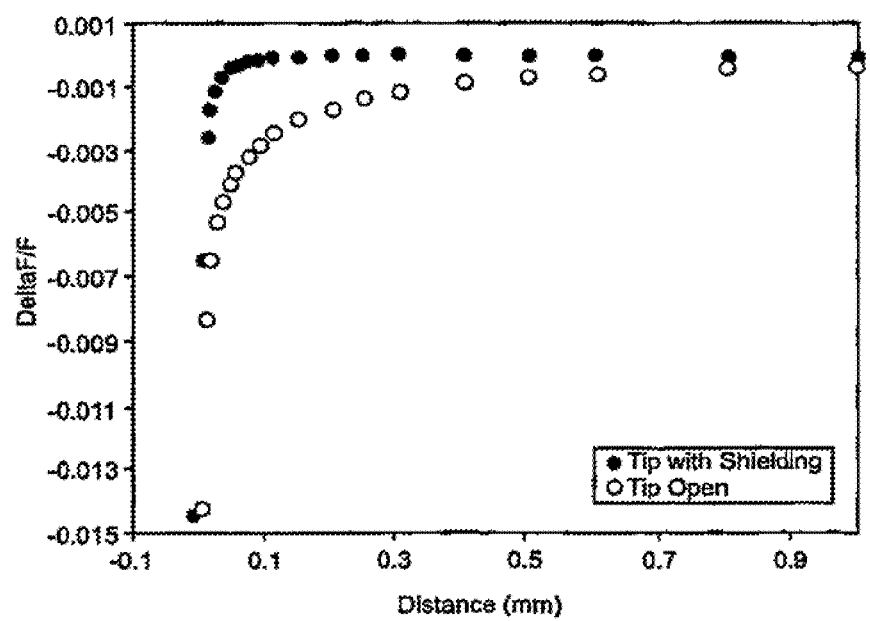

Exemplary data illustrating the effectiveness of shielding the tip is shown in FIGS. 33A-B. FIG. 33A is a graph of the resonant frequency change of an evanescent wave probe as the tip of the probe approaches a metal surface; the two curves of the graph (open circles and closed circles) are a comparison between an open tip, and a ground wire balanced tip such as the tip depicted in FIG. 11.

FIG. 33B is a graph of the resonant frequency change of an EWP as the tip approaches a metal surface; these two curves compare a probe having an open tip (open circles in the graph) and a probe having a tapered coaxial shielded tip (filled in circles). The dramatic difference between the two curves indicates that a coaxially shielded tip is influenced much less by far field effects, and thus has a much higher resolution.

EMP with Actively Controlled Feedback Loop

One side effect of the shielding design for an evanescent microwave probe (as used herein, the terms evanescent wave probe, or EWP, and evanescent microwave probe, or EMP will be used interchangeably) is a reduced signal-to-noise ratio. Shielding the probe in a manner consistent with any of the embodiments described above increases the close-distance-overlapping area between the center tip and the shielding, which increases the transition line loss as microwave current flows through these structures. The quality factor of the resonator decreases due to this extra loss, which in turn causes the signal-to-noise ratio of the probe to decrease.

To overcome this problem, an active feedback technique is introduced here to increase the signal-to-noise ratio of the EMP. Active feedback techniques in general are know in the art, and have been broadly used in the low frequency and RF detection as an effective way to increase the sensitivity. See, for example, T. R. Albrecht et al., J. Appl. Phys. 69, 668 (1991); U. Durig et al., J. Appl. Phys. 82, 3641 (1997); and K. Weyand, IEEE Trans. Instrum. Measurem., 38, 410 (1989).

Figure 34A:
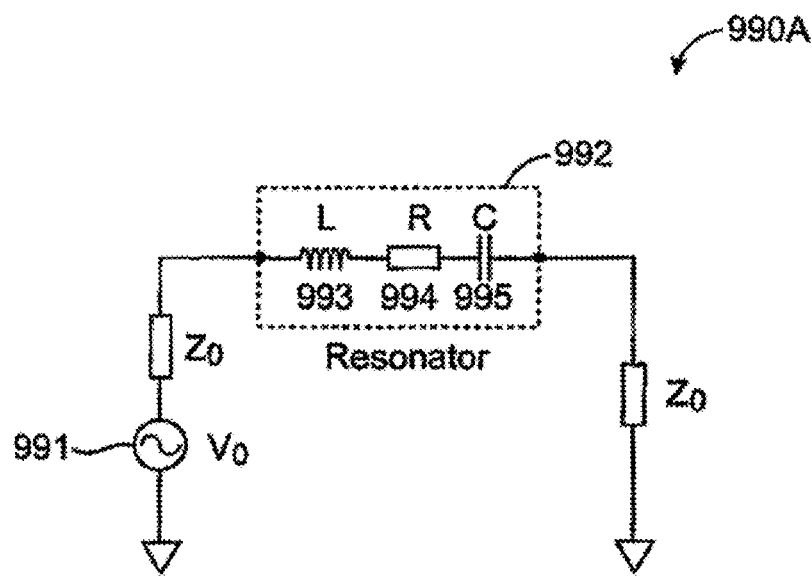
FIG. 34A is an equivalent circuit of a conventional resonator with a signal source and detector connected; the signal source has internal impedance $Z_0$ and signal amplitude $V_0$; the detector has impedance $Z_0$; and the equivalent inductance, capacitance and resistance of the resonator are L, C and R, respectively.

According to the present embodiments, an RF/microwave feedback loop is inserted between the input and output of the resonator. These concepts are illustrated schematically in FIGS. 34A-B. FIG. 34A is an equivalent circuit of conventional resonator shown generally at 990A, the conventional resonator having connected thereto a signal source 991 and detector. The signal source has internal impedance $Z_0$, typically about 50 ohms, and signal amplitude $V_0$; the detector has impedance $Z_0$; and the equivalent inductance 993, capacitance 994, and resistance 995 of the resonator 992 are L, C and R, respectively.

Figure 34B:
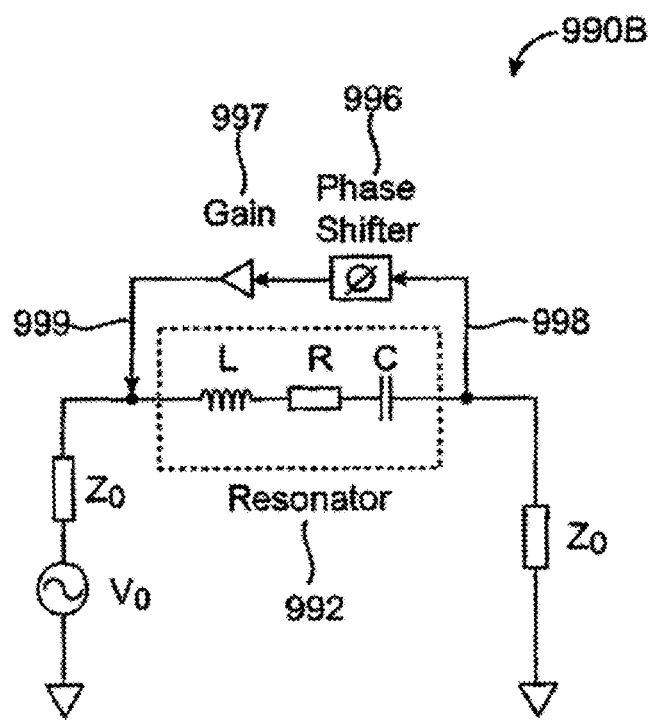
FIG. 34B is an equivalent circuit of an oscillator further including the inventive actively controlled feedback loop; in this embodiment the feedback loop comprises a resonator, a phase shifter and a gain amplifier.

FIG. 34B is an equivalent circuit of an oscillator further including the inventive actively controlled feedback loop; in this embodiment the feedback loop comprises a resonator 992, a phase shifter 996, and a gain amplifier 997 to comprise an actively controlled feedback loop 990B. The phase and gain of the feedback loop 990B are adjusted to values wherein both the intensity and effective quality factor of the original resonator 990A can be substantially increased. Increasing the intensity and effective quality factor of the resonator has the effect of improving the signal-to-noise ratio of the EWP.

Figure 35:
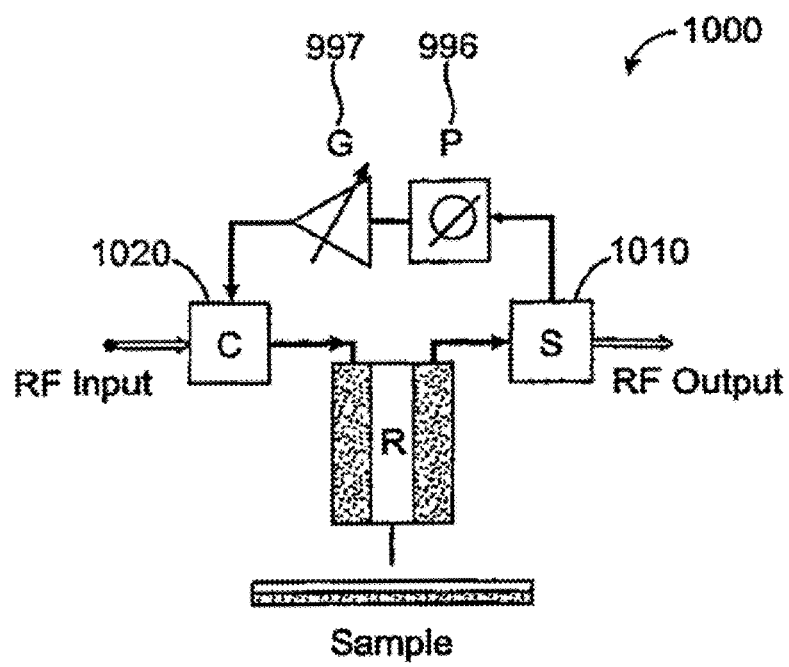
FIG. 35 is a schematic diagram of an exemplary EWP measurement system with the active feedback controlled resonator, further including a combiner and a splitter as part of the feedback loop.

Two ways in which an active feedback loop may be added to an EWP resonator will be discussed next. In the first approach, an active feedback loop is added to the resonator to form a passive device with an increased effective Q. When this approach is used, it is necessary to provide a microwave source to drive the resonator. FIG. 35 shows an embodiment of an EWP measurement system 100 with an active feedback controlled resonator, the feedback loop comprising a phase shifter 996 and gain amplifier 997, and further comprising a splitter 1010 and a combiner 1020. The electrical delay line or phase shifter 996 may be either fixed or variable, and is used to adjust the phase shift between the output port and input port of the resonator to 0° (which is the same thing as 360°) or any other phase for any special purpose. The RF amplifier 996 is adjusted to obtain a high Q value for the resonator.

Figure 36:
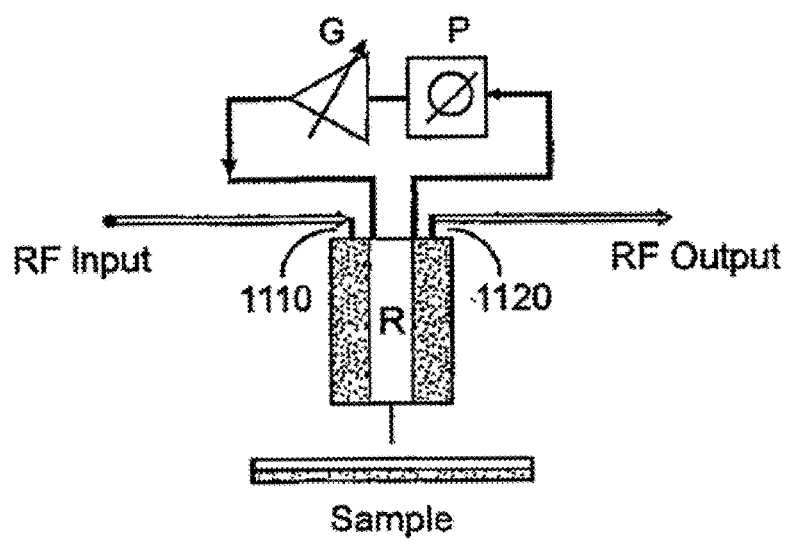
FIG. 36 is a schematic diagram of an exemplary EWP with an active feedback loop similar to that shown in FIG. 35, except that two coupling ports of the resonator have been used to replace the combiner and splitter of FIG. 35.

In a different configuration of the first way that an active feedback loop may be added to the EWP resonator, the splitter and combiner can be eliminated and replaced with two more resonator coupling ports 1110, 1120, as shown in FIG. 36. In either of these two configurations, the feedback loop may be integrated with the resonator, or setup as a separate structure from the resonator.

When measurements of impedance or magnetic susceptibility are desired, an input signal source is needed for excitation. If, on the other hand, it is desired to construct an electromagnetic field profile, then no input signal is required. The EWP tip (which may be configured either as an open tip or a loop tip) will pick up a local field signal proportional to the intensity of the field. The field components along different directions also can be mapped by implementing different orientations of the tip.

Figure 37:
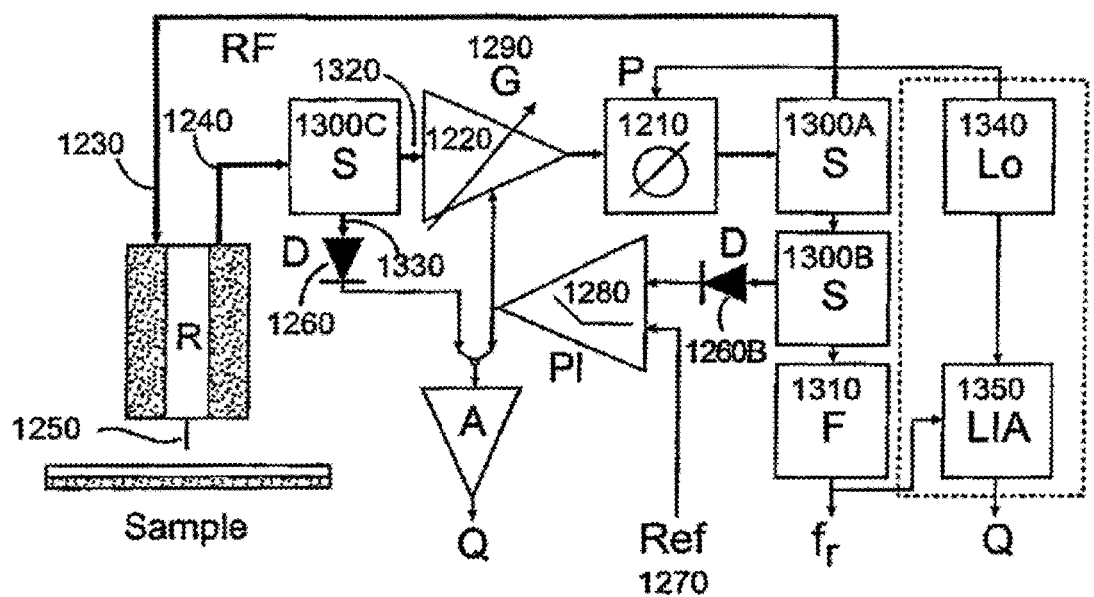
FIG. 37 is a schematic diagram of an exemplary EMP measurement system with an active resonator functioning in a self-oscillating mode.

In the second approach, an active feedback loop is added to the resonator to form a self-oscillator with an oscillating frequency substantially equal to, or close to, the original resonant frequency of the resonator. The driving microwave is no longer necessary in this method. FIG. 37 is an exemplary setup of such a system. A phase shifter 1210 and a variable gain amplifier 1220 is added between the input and output ports (1230, 1240, respectively) of the resonator to realize the positive feedback at or close to the original resonant frequency of the resonator such that the self-oscillation (RF) is generated inside the feedback loop and the probe tip 1250. To control the amplitude of the self-oscillation, the power of the microwave is measured by a diode detector 1260, and compared with a reference value 1270. The error signal is then processed by a proportional integral amplifier 1280 to adjust the gain of 1290 so that the microwave power is locked at a constant value. Several splitters 1300A, 1300B, 1300C are used in the microwave path in order to channel the microwave signal to different detectors.

Measuring the Complex Impedance of a Sample

Next, a discussion of the measurement of complex impedance will be given, again referring to the resonator with an active feedback loop of the second approach; that is to say, in the form of a self-oscillator, as shown in FIG. 37. Both the resonant frequency ($f_r$) and the quality factor (Q) of the active resonator need to be measured in order to calculate the complex impedance of the sample. The relationship of $f_r$, Q, and the sample impedance is well developed in the pervious art (see, for example, U.S. Pat. Nos. 6,173,604 and 6,532,806) and is not described here.

The resonant frequency is measured by the frequency detection electronics 1310, which can be any method commonly used in the art to measure a resonant frequency in the RF or microwave range, such as a digital frequency counter, a gated timer, a phase-locked loop, or various analog FM demodulator circuits.

There are also several ways to measure the Q of the resonator. Three will be discussed in this disclosure. A first method for measuring the Q of the resonator relies upon the fact that Q is a function of the microwave output power of the resonator at constant input power with fixed couplings. The higher the output power, the higher the Q. To implement this method, a splitter 1300C is used at the resonator output 1240 to separate the microwave signal evenly or unevenly into two paths. One path 1320 is for the active feedback loop. The other path 1330 transfers a portion of the signal to the diode detector 1260 to measure the power; this parameter is needed for the calculation of the Q of the resonator.

A second method for measuring Q makes use of the fact that since the output power of the resonator changes with the Q of the resonator, the gain of the variable gain amplifier 1290 will change correspondingly in order to keep the output power of the amplifier substantially constant. Therefore, the Q measurement may be effected by monitoring the feedback gain of the amplifier 1290. An advantage of this second method for measuring Q, relative to the first, is that this second method requires one less splitter 1300, and one less diode 1260B. However, an inherent disadvantage with this second method is that it may be more complicated to convert the gain value to Q, especially when the gain of the amplifier 1290 is nonlinearly proportional to its control voltage.

A third method for measuring Q involves an AC modulation technique. A low frequency AC signal is generated by a function generator 1340 to modulate the phase of the phase shifter 1210. This in turn induces a modulated shift on the resonant frequency, which may be detected by a lock-in amplifier 1350. Since the resonant frequency shift is proportional to the phase shift amplitude and inversely proportional to the Q of the resonator, the frequency modulation amplitude detected by the lock-in amplifier 1350 may be used to calculate the Q of the resonator. As long as the frequency detection circuit is fast enough, the AC modulation technique of this third method can provide the best sensitivity relative of the three methods.

Analysis of the Active Feedback Resonator

In this section, the operation of the active feedback resonator is analyzed for a resonator is being operated in a passive manner. The equivalent circuit of a conventional resonator was shown in FIG. 34A, the resonator having a signal source 991 and detector 992. Assuming the signal source 991 and the detector 992 have the same impedance $Z_0$, the signal across the detector $V_s$ under a driving voltage $V_0$, is, $$\frac{V_S}{V_0} = \frac{Z_0}{R + 2Z_0 + i\omega L + \frac{1}{i\omega C}} \quad (1)$$

$$= \frac{Z_0}{R + 2Z_0} \frac{1}{1 + 2iQ_l \frac{\Delta\omega}{\omega_0}}$$

where $\Delta\omega = \omega - \omega_0$, $\omega_0$ is the resonant frequency, and $Q_l$ is the loaded quality factor as defined below:

$$\omega_0 = \frac{1}{\sqrt{LC}} \quad (2)$$

$$Q_l = \sqrt{\frac{L}{C}} \frac{1}{R + 2Z_0} \quad (3)$$

When the present active feedback loop is added to the resonator circuit, as previously shown in FIG. 34B, the output signal 998 of the resonator is fed into the phase shifter 96 and an RF amplifier 997, and the output 999 of the RF amplifier is added back to the resonator's input port. The circuit may be analyzed theoretically as follows: assuming the output impedance of the amplifier is also $Z_0$, then, $$V_S = (V_0 + g e^{i\varphi} V_S) \frac{Z_0}{R + 2Z_0 + i\omega L + \frac{1}{i\omega C}}, \quad (5)$$

where g and $\varphi$ are the gain and phase shift of the feedback loop, respectively. Practically speaking, g and $\varphi$ may be adjusted from about 0 to 10,000 and 0° to 360°, respectively. By solving the above equation, it is possible to obtain:

$$\frac{V_S}{V_0} = \frac{Z_0}{R + 2Z_0 - gZ_0\cos(\varphi)} \frac{1}{1 + 2iQ'\frac{\Delta\omega}{\omega_0'}} \quad (4)$$

where $\Delta\omega = \omega - \omega_0'$, $\omega_0'$ and $Q'$ are the effective resonant frequency and quality factor, $$\frac{\omega_0'}{\omega_0} = \sqrt{1 + \alpha^2} + \alpha \quad (5)$$

$$Q' = \frac{\omega_0' L + \frac{1}{\omega_0' C}}{2(R + 2Z_0 - gZ_0\cos(\varphi))} \quad (6)$$

and $$\alpha = \frac{1}{2} gZ_0 \omega_0 C \sin(\varphi) \quad (7)$$

where $\omega_0$ is resonator's intrinsic resonant frequency when a feedback-loop is not present.

If $\varphi$ equals zero, it may be shown that:

$$\omega_0' = \omega_0 \quad (8)$$

$$Q' = Q_l \frac{1}{1 - gZ_0/(R + 2Z_0)}$$

$$\frac{V_S}{V_0} = \frac{Z_0}{R + 2Z_0} \cdot \frac{1}{1 - gZ_0/(R + 2Z_0)}$$

It will be understood by those skilled in the art that the quality factor has been increased by a factor of $$\frac{1}{1 - gZ_0/(R + 2Z_0)}.$$

Thus, it is possible to achieve an effective Q' much higher than the original $Q_1$ by adjusting the feedback gain g under the condition that $gZ_0/(R+2Z_0)<1$. Similarly, the output amplitude at the resonant frequency is increased by the same factor. The increase in both Q and the amplitude will improve the signal-to-noise ratio of the resonator. A further point to be made is that if the condition $gZ_0/(R+2Z_0)\geq 1$ exists, then a self-oscillating condition appears in the feedback loop, and when this happens, it is no longer advisable to use the device in a passive mode. This is not to say that the device cannot be used in a self-oscillation mode; in fact it can, as will be described later.

It will be understood by one skilled in the art that when $\varphi$ is not zero in equations 5 and 7, the resonator can be tuned to specified resonant frequency and quality factor by choosing appropriate values for $\varphi$ and g. Furthermore, if p and/or g are functions of frequency, expressed mathematically as $\varphi(\omega)$ and/or $g(\omega)$, it is possible to influence the spectral shape of either the resonator output amplitude or phase. For example, inside the bandwidth, by making the gain g lower at a resonant frequency $\omega_0'$ and higher for any other frequency, to is possible to obtain a flat output inside the bandwidth. This feature provides the potential for an application that uses an active resonator as a tunable band-pass filter.

When the active resonator is working in self-oscillating mode, the microwave source is no longer necessary to provide the driving signal. The self-oscillation in the loop maintains its oscillation under a fixed resonant frequency. This mode may be analyzed again with the equivalent circuit shown in FIG. 34B, but with the input impedance $Z_0$ becoming infinitely large and the driving signal $V_0$ going to zero. In this case, the equation (1) shown previously for $V_s/V_0$ is no longer meaningful, since $V_0$ is now zero. However, it is possible to use a transfer function $T(\omega)$ to describe the system, wherein the transfer function may be expressed as:

$$T(\omega) = \frac{1}{1 + \frac{R}{Z_0} - g\cos(\varphi)} \cdot \frac{1}{1 + 2iQ'\frac{\Delta\omega}{\omega_0'}} \quad (9)$$

with $\Delta\omega = \omega - \omega_0'$, $\omega_0'$ defined as the same quantity as previously shown in equations (5) and (7). The effective quality factor Q' is different from the definition in equation (6) since the input impedance is no longer there:

$$Q' = Q_l \frac{\frac{1}{2}\left(\frac{\omega_0'}{\omega_0} + \frac{\omega_0}{\omega_0'}\right)}{\left(1 - \frac{g\cos(\varphi)}{1 + \frac{R}{Z_0}}\right)} \quad (10)$$

$$Q_l = \sqrt{\frac{L}{C}} \frac{1}{R + Z_0} \quad (11)$$

Similar to the previous situation, where the resonator was being operated in a passive mode as described by equations (6) and (8), in this case of the resonator acting as a self-oscillaror, Q' is increased by a factor of $$\frac{1}{1 - \frac{g\cos(\varphi)}{1 + R/Z_0}}$$

relative the original $Q_1$. As before, this increase in Q' can substantially increase the signal-to-noise ratio of the resonator.

According to equation (9), the resonator self-oscillates when $T(\omega)$ goes to infinity while its imaginary part is zero. Such a condition may be expressed equivalently by the following equation:

$$1 + \frac{R}{Z_0} = g\cos(\varphi) \quad (12a)$$

$$\omega = \omega_0' = \omega_0\left(\sqrt{1+\alpha^2} + \alpha\right) \quad (12b)$$

where α is defined by equation (7)

The amplitude condition described by equation (12a) ensures that the oscillation amplitude is constant. This function is performed by the auto-gain control circuit, as described by the disclosure of FIG. 37. The phase condition exemplified by equation (12b), on the other hand, determines the frequency of the self-oscillation. Understanding that the phase shift between the input and output ports of the resonator $\Phi_r=0$ at the resonator's resonant frequency, it will be apparent to one skilled in the art that the oscillation frequency ($\omega_0'$) is, in general, different from the resonant frequency ($\omega_0$) of the resonator unless the phase of the feedback amplifier ($\phi$) matches the phase $\Phi_r$.

To understand the phase condition in more detail, equation (12b) may be expressed in a simpler form. The first step is to rewrite equation (7) as:

$$\alpha = \frac{1}{2Q_l} \cdot \frac{g}{1 + \frac{R}{Z_0}} \sin(\varphi) \quad (13a)$$

Under self-oscillation, where equation (12a) applies, the parameter a may be written as:

$$\alpha = \frac{1}{2Q_l} \cdot \tan(\varphi) \quad (13b)$$

In most of cases, $Q_1 \gg 1$, and equation (12b) may therefore be expressed as:

$$\omega = \omega_0' \approx \omega_0\left(1 + \frac{1}{2Q_l}\tan(\varphi)\right) \quad (14)$$

This new resonant frequency is a function of $Q_1$ and $\phi$. If a modulation signal is imposed on $\phi$, and the relative frequency modulation is detected through the lock-in amplifier 1350, the $Q_1$ of the resonator may be calculated though the phase derivative of equation (14), with very high sensitivity. It may also be seen from equation (10) that under oscillation the Q' becomes infinitely large under the conditions of equation (12a). It will be readily apparent to those skilled in the art that a resonator with a narrow resonant peak be very sensitive to the frequency change.

Theoretical analysis shows that the sensitivity of an EWP-based instrument is proportional to the Q of the resonator. High sensitivity may be achieved by using an EWP resonator with a high Q. In most cases, the Q of the resonator is limited by the microwave energy loss on the metal conductors that make up the resonator. In order to achieve a high Q for a resonator, it is preferable to utilize high conductivity metal parts within the resonator, and preferably the dimensions of the resonator are designed to be large. Practically speaking, the Q of the resonator ranges from about one hundred to three thousand.

In many situations resonators having small dimensions are desired and/or required, in which case the Q of the resonator may be relatively low. Such a resonator may be used with the present active feedback loop to increase the quality factor of EWP resonator, and thus increase the instrument's sensitivity. Typical, the amount that the quality factor is increased from Q to Q' by the active feedback technique is in a range from about 1 to 10,000. Inclusion of the present active feedback loop also makes it possible to decrease the EMP probe size, in some instances dramatically, to therefore enable the integration of EMP with AFM, STM, MFM or other microscope devices.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. An evanescent wave probe configured to detect spin resonance from at least one member of an array of catalysts in a catalyst library, wherein the configuration comprises a resonator having a signal source and a resonance detector, wherein the evanescent wave probe is integrated with a scanning probe microscope to regulate the distance between the evanescent wave probe and the at least one member of the catalyst library.

2. The evanescent wave probe of claim 1, wherein the spin resonance is electron spin resonance (ESR).

3. The evanescent wave probe of claim 1, wherein the spin resonance is nuclear magnetic resonance (NMR).

4. An evanescent wave probe configured to detect spin resonance from at least one member of an array of micro-reactors in a micro-reactor library, wherein the configuration comprises a resonator having a signal source and a resonance detector, wherein the evanescent wave probe is integrated with a scanning probe microscope to regulate the distance between the evanescent wave probe and the at least one member of the micro-reactor library.

5. The evanescent wave probe of claim 4, wherein the spin resonance is electron spin resonance (ESR).

6. The evanescent wave probe of claim 4, wherein the spin resonance is nuclear magnetic resonance (NMR).

7. The evanescent wave probe of claim 1, wherein the scanning probe microscope is selected from the group consisting of an atomic microscope and a scanning tunneling microscope.

8. The evanescent wave probe of claim 4, wherein the scanning probe microscope is selected from the group consisting of an atomic force microscope and a scanning tunneling microscope.

\* \* \* \* \*

UNITED STATES PATENT AND TRADEMARK OFFICE
CERTIFICATE OF CORRECTION

| | |
|---|---|
| PATENT NO. | : 7,704,923 B2 |
| APPLICATION NO. | : 11/299034 |
| DATED | : April 27, 2010 |
| INVENTOR(S) | : Xiao-Dong Xiang et al. |

It is certified that error appears in the above-identified patent and that said Letters Patent is hereby corrected as shown below:

In Claim 7, at column 38, line 53, insert --force-- between "atomic" and "microscope".

Signed and Sealed this
Twenty-first Day of June, 2011

David J. Kappos
*Director of the United States Patent and Trademark Office*